(12) United States Patent
Young

(10) Patent No.: US 11,752,340 B2
(45) Date of Patent: Sep. 12, 2023

(54) INTRAVAGINAL ELECTRICAL STIMULATION DEVICE FOR TREATING FEMALE PELVIC PAIN

(71) Applicant: IVES, LLC, Annapolis, MD (US)

(72) Inventor: Erik B. Young, Annapolis, MD (US)

(73) Assignee: Ives, LLC, Annapolis, MD (US)

( * ) Notice: Subject to any disclaimer, the term of this patent is extended or adjusted under 35 U.S.C. 154(b) by 10 days.

(21) Appl. No.: 17/504,689

(22) Filed: Oct. 19, 2021

(65) Prior Publication Data

US 2022/0126097 A1 Apr. 28, 2022

Related U.S. Application Data

(60) Provisional application No. 63/104,588, filed on Oct. 23, 2020.

(51) Int. Cl.
*A61N 1/36* (2006.01)
*A61N 1/05* (2006.01)
*A61N 1/372* (2006.01)

(52) U.S. Cl.
CPC ....... *A61N 1/36071* (2013.01); *A61N 1/0524* (2013.01); *A61N 1/36128* (2013.01); *A61N 1/37223* (2013.01); *A61N 1/37235* (2013.01)

(58) Field of Classification Search
CPC ............... A61N 1/0456; A61N 1/0524; A61N 1/36021; A61N 1/36071; A61N 1/36128;
(Continued)

(56) References Cited

U.S. PATENT DOCUMENTS 4,106,511 A 8/1978 Erlandsson
4,580,578 A 4/1986 Barsom
(Continued)

FOREIGN PATENT DOCUMENTS

CN 104436437 A 3/2015
CN 206518771 U 9/2017
(Continued)

OTHER PUBLICATIONS

Allon, the role of neuromuscular electrical stimulation in the rehabilitation of the pelvic floor muscles, British Journal of Nursing, vol. 28, No. 15, pp. 968-974, 2019.
(Continued)

*Primary Examiner* — Amanda K Hulbert
(74) *Attorney, Agent, or Firm* — Grady L. White; Potomac Law Group, PLLC

(57) ABSTRACT

An intravaginal electrical stimulation device for treating pelvic pain in a female patient comprises a set of intravaginal components and an external controller. The intravaginal components include a frame, at least one pair of paracervical electrodes embedded in the proximal portion of the frame, an intravaginal capsule, an electrode plug that plugs into a socket in the proximal end of the capsule, and connecting wires that electrically couple the electrode plug to the paracervical electrodes. The intravaginal components are designed to inserted into the patient's vagina so that the paracervical electrodes are in direct contact with the vaginal epithelium in the lateral vaginal fornices. Electronics, including a microprocessor and an electrical stimulation generator, are configured to generate and transmit low-voltage electrical current to the paracervical electrodes to create an electrical field that neuromodulates the pelvic and paracervical nerves, the nerves that innervate the uterus, and other anatomical structures of the lower pelvis, which tends to reduce or eliminate pelvic pain. The set intravaginal components are configured so that a woman can easily insert them into her vagina (with or without a medical practitioner being present). The external controller, which communicates with the intravaginal components over a wireless data communication channel, sends instructions to and receives status updates from the microprocessor inside the intravaginal capsule. The external controller may be operated by the
(Continued)

female patient to control the electrical profile (e.g., frequency, amplitude and duration) of the electrical stimulation delivered to her body, and thereby cause the intravaginal components to deliver well-controlled, personalized, electrical stimulation to her pelvic and paracervical nerves when she is experiencing pain, or when she anticipates the onset of pelvic pain due to, for example, menstruation or sexual intercourse.

22 Claims, 30 Drawing Sheets

(58) Field of Classification Search
CPC ............ A61N 1/37211; A61N 1/37223; A61N 1/37235
See application file for complete search history.

(56) References Cited

U.S. PATENT DOCUMENTS

| | | | |
|---|---|---|---|
| 5,800,501 | A | 9/1998 | Sherlock |
| 5,871,533 | A | 2/1999 | Boutos |
| 6,055,456 | A | 4/2000 | Gerber |
| 6,185,465 | B1 | 2/2001 | Mo et al. |
| 8,634,920 | B2 | 1/2014 | Hagege |
| 8,644,938 | B2 | 2/2014 | Craggs |
| 8,805,509 | B2 | 8/2014 | Boyd et al. |
| 8,914,111 | B2 | 12/2014 | Haessler |
| 9,358,383 | B2 | 6/2016 | Boyd et al. |
| 9,737,707 | B2 | 8/2017 | Haessler et al. |
| 9,999,490 | B2 | 6/2018 | Rosen et al. |
| 10,016,599 | B2 | 7/2018 | Lockwood et al. |
| 10,105,531 | B2 | 10/2018 | White et al. |
| 11,027,120 | B2 | 6/2021 | Peddicord |
| 11,110,269 | B2 | 9/2021 | Gregson |
| 2011/0009692 | A1 | 1/2011 | Gross |
| 2014/0058474 | A1 | 2/2014 | Haessler |
| 2017/0065222 | A1 | 3/2017 | Egorov |
| 2018/0185641 | A1 | 7/2018 | Peled |
| 2021/0030464 | A1 | 2/2021 | Na |

FOREIGN PATENT DOCUMENTS

| | | |
|---|---|---|
| CN | 206631014 U | 11/2017 |
| EP | 0963217 B1 | 12/2004 |
| JP | 3125942 U | 10/2006 |
| JP | 2018064727 A | 4/2018 |
| KR | 200254852 Y1 | 12/2001 |
| WO | 9517922 A2 | 7/1995 |
| WO | 1995017922 A2 | 7/1995 |
| WO | 2012058289 A2 | 5/2012 |
| WO | 2013185121 A1 | 12/2013 |

OTHER PUBLICATIONS

Boston Scientific, "mySCS a Personalized and Connected SCS Experience," product brochure, https://www.bostonscientific.com/en-US/products/spinal-cord-stimulator-systems/myscs.html, 2021.
Boston Scientific, "Precision Novi Primary Cell Spinal Cord Stimulator System," product brochure, https://www.bostonscientific.com/en-US/products/spinal-cord-stimulator-systems/precision_novi.html, 2021.
Boston Scientific, "SCS Competitive Adapters & Connectors," product brochure, https://www.bostonscientific.com/en-US/products/spinal-cord-stimulator-systems/adapters-and-connectors.html, 2021.
Boston Scientific, "SCS Lead Portfolio," product brochure, https://www.bostonscientific.com/en-US/products/spinal-cord-stimulator-systems/scs_lead_portfolio.html, 2021.
Boston Scientific, "Spectra WaveWriter, Spinal Cord Stimulator System," product brochure, https://www.bostonscientific.com/en-US/products/spinal-cord-stimulator-systems/spectra-wavewriter.html, 2021.
Lempka et al., "Innovations in spinal cord stimulation for pain," Curr. Opin. Biomed. Eng., vol. 8, pp. 51-60, Dec. 2018.
McKenzie-Brown, "Spinal cord stimulation: Placement and Management," UpToDate, 2020, https://www.uptodate.com/contents/spinal-cord-stimulation-placement-and-management/print?source=autocomplete&index=0~2&search=spinl%5Cal%E2%80%A6.
Unkown, "Sacral nerve stimulation," Wikipedia, Feb. 2021.

Midline Sectional View of a Human Female Pelvis

Intravaginal Capsule (IVC) - Orthogonal Cross-Section View

Intravaginal Capsule (IVC) - Distal End On View

Intravaginal Capsule (IVC) - Proximal End On View

Positioning of the paracervical electrodes in an embodiment of the IVES device where one pair of electrode units creates a single electrical stimulation circuit Positioning of the paracervical electrodes when two pairs of electrode units are used to create two electrical stimulation circuits

INTRAVAGINAL ELECTRICAL STIMULATION DEVICE FOR TREATING FEMALE PELVIC PAIN

FIELD OF THE INVENTION

Embodiments of the present invention relate generally to methods and devices for treating pelvic pain in women, and more particularly to methods and devices that provide electrical stimulation to the neural structures in the pelvis, including the nerves that traverse ligaments in the pelvic floor that support the uterus and the uterine cervix, and nerve fibers in the neural ganglia in the pelvis, such as the uterovaginal ganglion. These neural structures transmit pain signals from the uterus and other organs in the pelvis to the central nervous system.

BACKGROUND OF THE INVENTION

Many women suffer from chronic pelvic pain. Causes of chronic pelvic pain in women include, for instance, pelvic adhesions (scarring following surgery or pelvic infection), interstitial cystitis/bladder pain syndrome, neuropathic pain, myofascial or musculoskeletal pain and post-surgical pain. Some women experience idiopathic pelvic pain, which is pelvic pain resulting from unknown and/or undiagnosed causes.

Dysmenorrhea is the medical term for pelvic pain associated with menstruation. Primary dysmenorrhea refers to pain that occurs during menstruation that is not associated with an identified disorder of a woman's reproductive organs. Secondary dysmenorrhea is the medical term for pain that occurs during menstruation that is associated with a disorder in a woman's reproductive organs. The principal causes of secondary dysmenorrhea are endometriosis, adenomyosis, and uterine fibroids. Studies have shown that up to five million women in the United States and up to 140 million women worldwide suffer from dysmenorrhea when they are menstruating. Dyspareunia is the medical term for pelvic pain that is provoked by or exacerbated by sexual contact or sexual intercourse.

When pelvic pain caused by dysmenorrhea, dyspareunia or disorders that cause chronic pelvic pain is severe, many women have significant interruptions to their daily lives, including interference with their ability to work, study, and care for themselves and their loved ones. Some women experience long-term problems with their social, sexual, and psychological well-being due to the pain, and sometimes the pain can lead to recurring bouts of depression, anxiety, emotional distress and low self-esteem.

Medicinal treatment therapies for pelvic pain typically involve hormonal therapy, non-addictive and addictive pain relievers, antidepressants, and drugs designed to treat peripheral neuropathy. Non-medicinal therapies may include the application of heating pads, hot water bottles or cold compresses to the lower abdomen or lower back. These non-medicinal therapies are typically inconvenient and cumbersome.

Transcutaneous electrical nerve stimulation ("TENS") devices, which provide electrical stimulation to the lower abdomen or back via electrodes attached to the skin, have been used to treat dysmenorrhea and pelvic pain. However, the ability of TENS devices to successfully deliver timely and effective relief from pelvic pain on a consistent and reliable basis has been extremely limited because the areas of the body that are being stimulated are far removed from the neural pathways that need to be stimulated to get effective pelvic pain relief.

Accordingly, there is considerable need for devices and methods that provide more direct and more effective stimulation of the neural pathways associated with pelvic pain.

BRIEF SUMMARY OF EXEMPLARY EMBODIMENTS OF THE INVENTION

The pain associated with dysmenorrhea, dyspareunia and chronic pelvic pain typically originates in the uterus and other organs in the pelvis. The sensation of this pain is transmitted through numerous neural structures in the pelvis, including sympathetic, parasympathetic, and visceral sensory nerve fibers, many of which traverse ligaments in the pelvic floor supporting the uterine cervix and upper vagina, including the cardinal ligaments (See FIG. 3B). These supporting ligaments attach to the uterus just above (superior to) the area where the vaginal epithelium joins the uterine cervix (the "paracervical vaginal epithelium") in the vaginal fornices. The application of electrical stimulation to the paracervical vaginal epithelium using embodiments of the present invention is highly desirable and beneficial because the treatment is directly targeted to cause neuromodulation of the neural structures in the pelvis (hereinafter the "pelvic nerves"), including the nerves that traverse ligaments in the pelvic floor that support the uterus and the uterine cervix, and nerve fibers in the neural ganglia in the pelvis, such as the uterovaginal ganglion (hereinafter the "paracervical nerves"). The pelvic and paracervical nerves send pain signals from the uterus and other organs in the pelvis to the central nervous system and the neuromodulation of the pelvic and paracervical nerves may reduce or eliminate the sensation of pelvic pain.

Embodiments of the present invention overcome the aforementioned drawbacks associated with currently available nerve stimulation devices by providing an intravaginal electrical stimulation device (hereinafter referred to as an "IVES device"). Beneficially, the IVES device of the present invention is configured so that a woman can easily insert a set of intravaginal components of the IVES device into her vagina (with or without a medical practitioner being present) and activate the device with an external controller to cause the set of intravaginal components to deliver well-controlled, personalized, electrical stimulation (in the form of low-voltage electrical current) to the pelvic and paracervical nerves when she is experiencing pain, or when she anticipates the onset of pelvic pain due to, for example, menstruation or sexual intercourse. Electrical stimulation applied to the pelvic and paracervical nerves using embodiments of the present invention causes neuromodulation of these nerves, resulting in a reduction or elimination of pelvic pain.

In general, IVES devices configured to operate according to embodiments of the present invention comprise a set of intravaginal components and an external controller. The intravaginal components include a frame, one or more pairs of paracervical electrodes embedded in the surface material covering the proximal portion of the frame, a sling attached to and suspended from the frame, an intravaginal capsule (hereinafter referred to as the "IVC"), an intravaginal capsule pouch ("IVC pouch"), molded into the sling, and configured to receive and hold the distal end and middle portion of the IVC, a socket in the proximal end of the IVC, an electrode plug that plugs into the IVC socket in the proximal end of the IVC, and one or more connecting wires that electrically couple the electrode plug in the IVC socket to the paracervical electrodes embedded in the surface material of the proximal portion of the frame. During use, the frame of the IVES device is inserted into the vagina of the user so that the paracervical electrodes are in direct contact with the lateral vaginal fornices of the vagina. The IVC contains electronic components, including a microprocessor and an electrical stimulation generator, that together are configured to generate electrical stimulation (e.g., low-voltage electrical current) that is then transmitted to the paracervical electrodes via the electrode plug and connecting wire(s) to create an electrical field in the spaces in between and around the paracervical electrodes. The electrical field created between and around the paracervical electrodes neuromodulates pelvic and paracervical nerves, the nerves that innervate the uterus, and other neural structures of the pelvis. This neuromodulation tends to reduce or eliminate pelvic pain.

The external controller, which may comprise a personal computer, tablet computer, smart phone or other data processing or communication device, may be operated by the female patient to activate, deactivate and control the electrical profile (e.g., frequency, amplitude and duration) of the electrical stimulation delivered to the user's body by the electrical stimulation generator and the paracervical electrodes. To enable these neuromodulation control functions, the external controller comprises a microprocessor, a memory, a computer program (hereinafter referred to as the "IVES device remote control application" or the "IVES app") stored in the memory and a radio frequency transceiver. The IVES app contains program instructions executable by the microprocessor in the external controller. Operating under the control of the IVES app and the microprocessor, the radio frequency transceiver is configured to establish a wireless data communication channel with a second radio frequency transceiver located inside the IVC of the intravaginal component of the IVES device. The IVES app also comprises program instructions that, when executed by the microprocessor on the external controller, will cause the microprocessor use the radio frequency transceiver in the external controller to send instructions to and receive status updates from the microprocessor inside the IVC via the wireless data communications channel established between the two radio frequency transceivers.

A user interface module in the IVES app is configured to interact with the display screen on the external controller to permit the user to activate, adjust and tune the electrical stimulation generated and delivered to the paracervical electrodes by the electrical stimulation generator. Thus, the program instructions in the user interface module of the IVES app are suitably configured to allow the patient to manipulate controls (such as digital representations of buttons, icons and sliders) displayed on the display screen of the external controller in order to select, personalize, optimize, adjust, save, recall, activate and/or deactivate the settings and/or profile of the electrical stimulation delivered to the pelvic and paracervical nerves by the electrical stimulation generator in the IVC. In addition, the radio frequency transceiver and the microprocessor inside the external controller can request data and status information from the microprocessor and/or the memory of the IVC, and receive the data and status information over the wireless communication channel. The status information and other data may be displayed on the display screen associated with the external controller via the user interface. Preferably, the user interface for the IVES app running on the external controller also includes program instructions configured to permit the external controller or the user to use email, text messaging or another data transmitting process to send the status information and other data retrieved from the memory of the IVC to other devices, organizations or people, such as, for example, the user's personal physician or other health care provider.

Preferably, the IVES app stored in the memory of the external controller also includes program instructions that permit the external controller to periodically query a remote computer system or server to determine (1) whether any program updates associated with the IVES app running on the external controller are available, and/or (2) whether operating system updates, local program updates or firmware updates associated with the local control program stored in the memory of the IVC 102 are available. If such an update is available, the IVES app may be configured to automatically download and install the update on the external controller, on the IVC, or both. By downloading such updates as they become available, the control application program running on the external controller, as well as the operating system, application program and firmware running on the IVC will automatically remain substantially up-to-date with the latest bug fixes and/or improvements. In some embodiments, the IVES app may be configured to prompt the user for permission or confirmation before downloading and/or installing program, operating system or firmware updates.

DETAILED DISCUSSION OF EXEMPLARY EMBODIMENTS

Anatomical Terminology

Figure 1:
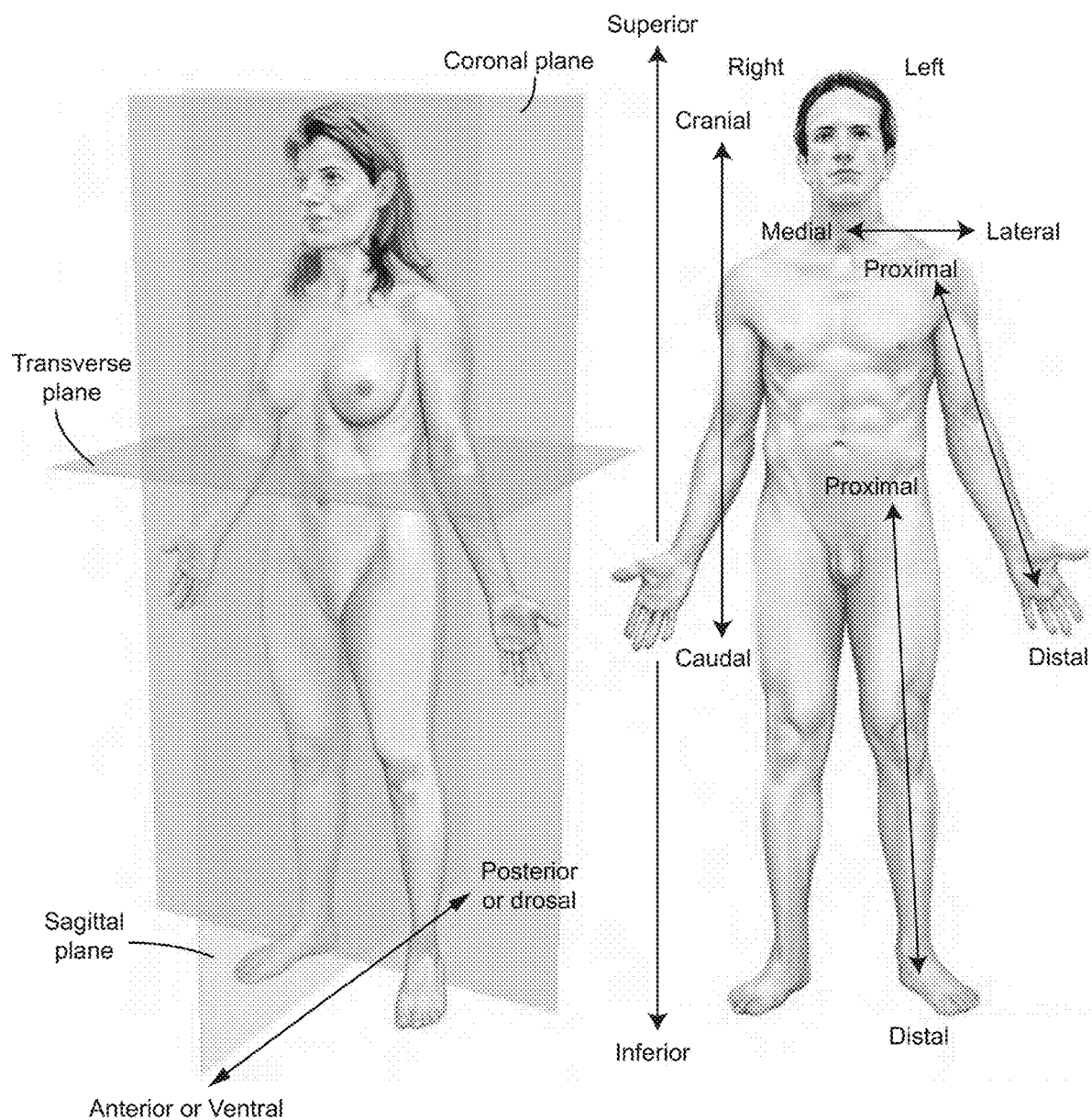
FIG. 1 shows anatomical diagrams of a woman and a man illustrating the conventional terms used to identify and describe the parts and planes of the human body, and the relationships therebetween.

FIG. 1 shows anatomical diagrams of a woman and a man illustrating the conventional terms used to identify and describe the parts and planes of the human body, and the relationships between those parts and planes. An anatomical plane (or anatomical section) refers to a view of anatomical structures in reference to a certain plane. For example, the median plane (or midline section) is a vertical plane that passes through the body longitudinally, front to back, dividing the body into equal right and left halves. A sagittal plane is any vertical plane passing through the body that is parallel to the median plane. Sagittal planes divide the body into right and left parts. Therefore, the midline plane is a sagittal plane, but a sagittal plane need not be the midline plane. The coronal planes, also called the frontal planes, are vertical planes passing through the body, from one side to the opposite side, dividing the body into an anterior (front) portion and a posterior (back) portion. These vertical planes are at right angles (90°) to the median and sagittal planes. Transverse planes are horizontal planes passing through the body, dividing it into superior (upper) and inferior (lower) parts. Transverse planes are at right angles (90°) to the median, sagittal and coronal planes. A superior view (sometimes called a "top view" or "bird's-eye" view) is a view that shows how a body part (such as an organ, nerve, ligament or cavity) would appear if looking down on it from a location above the body part, and the body part is properly oriented within the body. An inferior view (sometimes called a "bottom view") is a view that shows how a properly oriented body part would appear if looking up at it from a location below the body part.

Pelvic Anatomy

Figure 2:
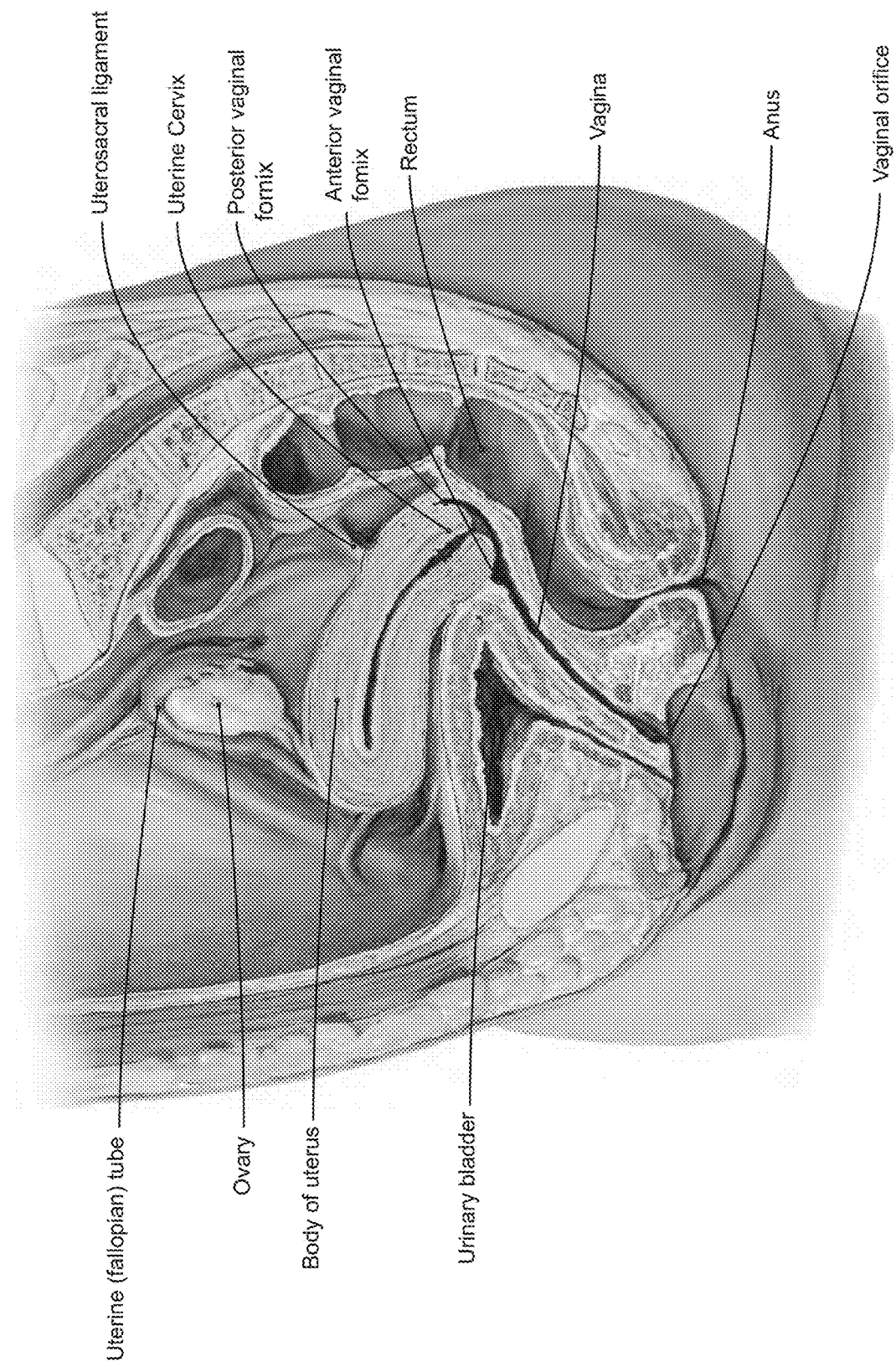
FIG. 2 shows an illustration of a midline sectional view of a human female pelvis and the location of female anatomical structures within the pelvis.
Figure 3A:
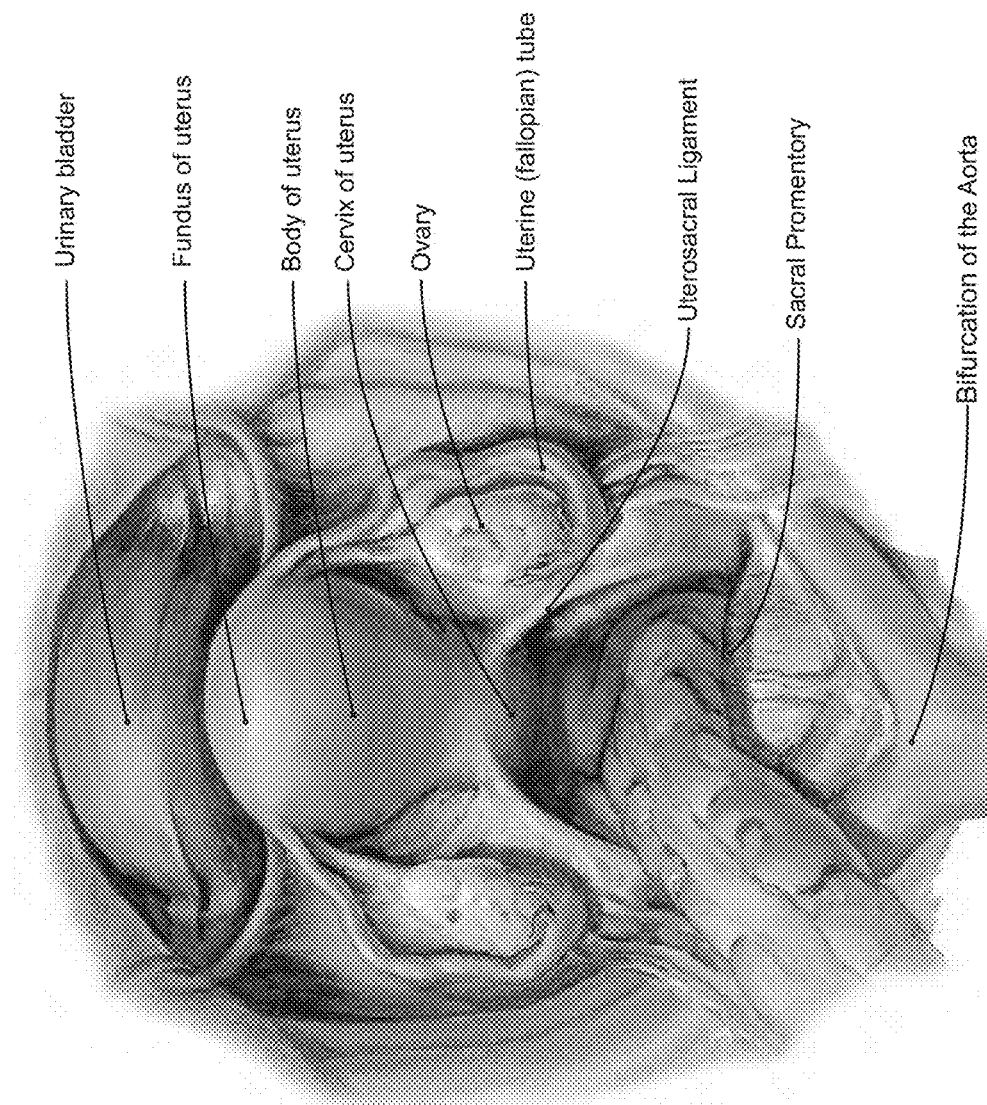
FIG. 3A shows an illustration of a superior view of the pelvic viscera (as visualized from within the abdomen)
Figure 3B:
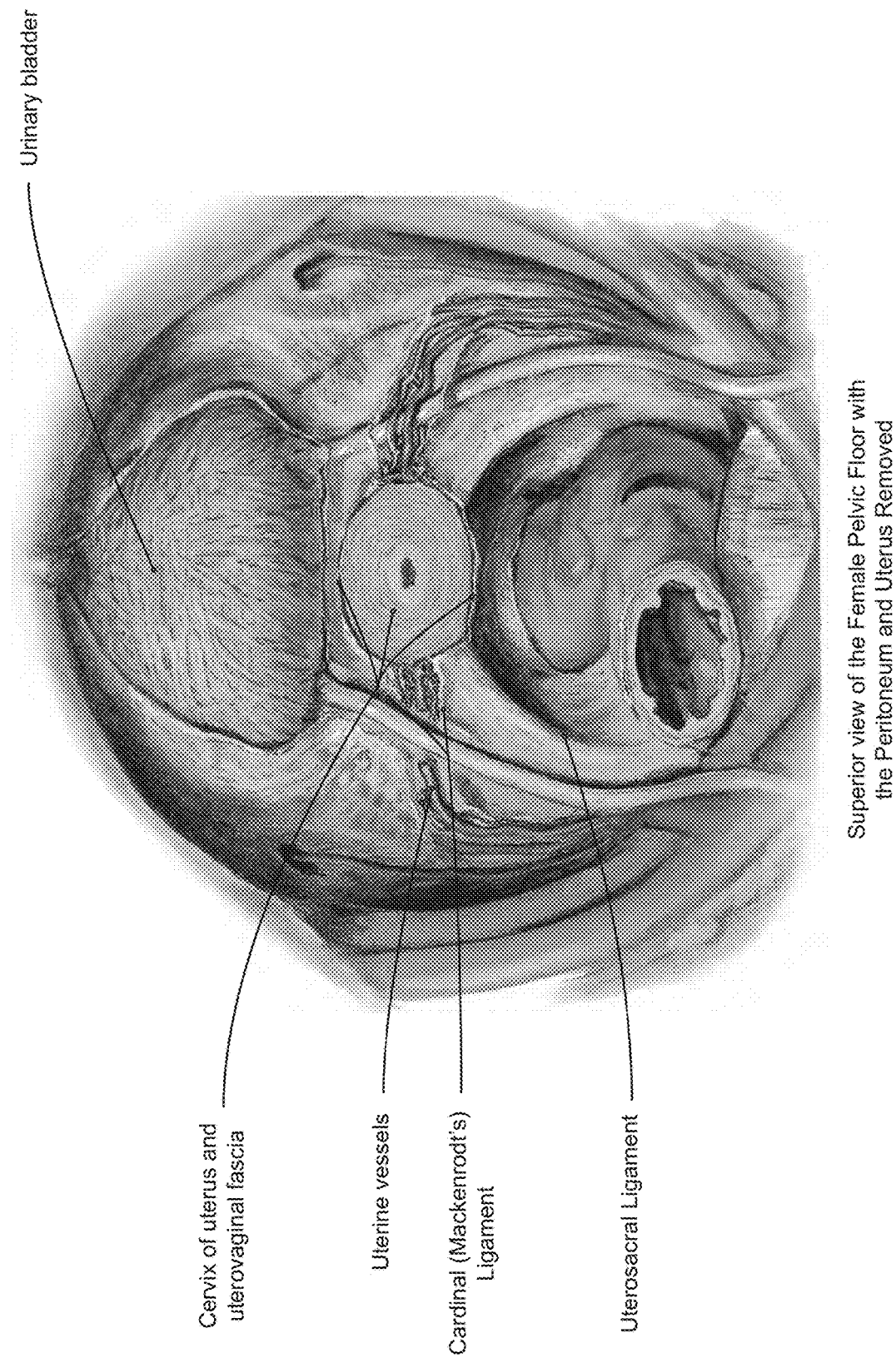
FIG. 3B shows an illustration of a superior view of the pelvic floor with the peritoneum and uterus removed (as visualized from within the abdomen).

FIG. 2 shows an illustration of a midline sectional view of a human female pelvis. The pelvis is the lower part of the abdomen that is below the rim of the pelvic bones. FIG. 3A shows an illustration of a superior view of the pelvic viscera (as visualized from within the abdomen), and FIG. 3B shows an illustration of a superior view of the pelvic floor with the peritoneum and uterus removed (as visualized from within the abdomen). As shown in FIGS. 2, 3A and 3B, the female pelvic viscera (or organs) that lie within the pelvis are the uterine fundus (the upper portion of the uterus), fallopian tubes and ovaries. These organs are located above, and supported by, the endopelvic fascia and ligaments that create the pelvic floor. The female viscera that lie below the pelvic floor include the uterine cervix, vagina, urethra, bladder and the lowermost part of the rectum.

Intravaginal Electrical Stimulation Device for Treating Female Pelvic Pain

Figure 23:
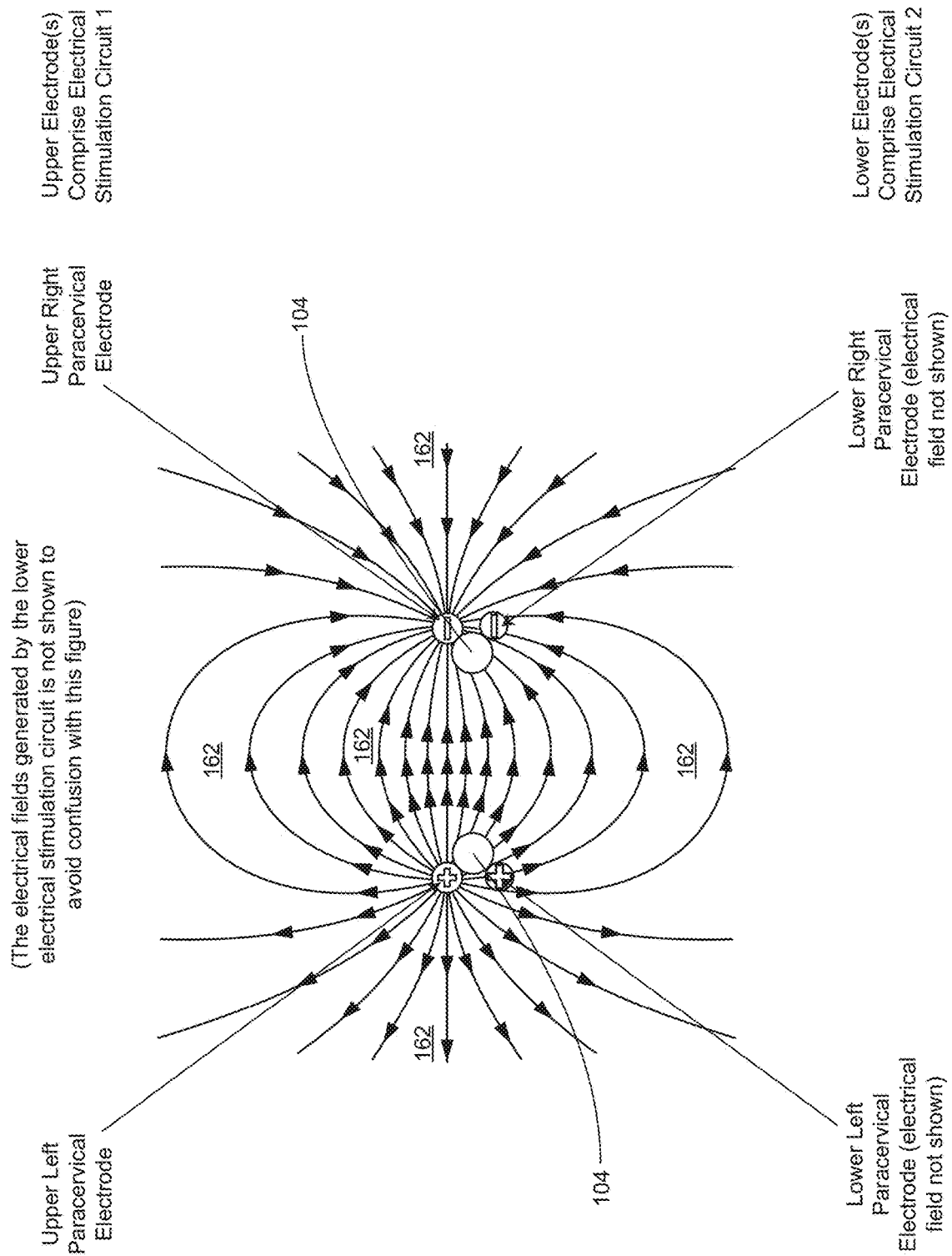
FIG. 23 shows a schematic representation of one of the two electrical fields generated by two electrical stimulation circuits with two pairs of paracervical electrodes positioned as shown in FIGS. 21A and 21B if the positive electrode and the negative electrode of each electrical stimulation circuit are located on opposite sides of the frame.
Figure 24:
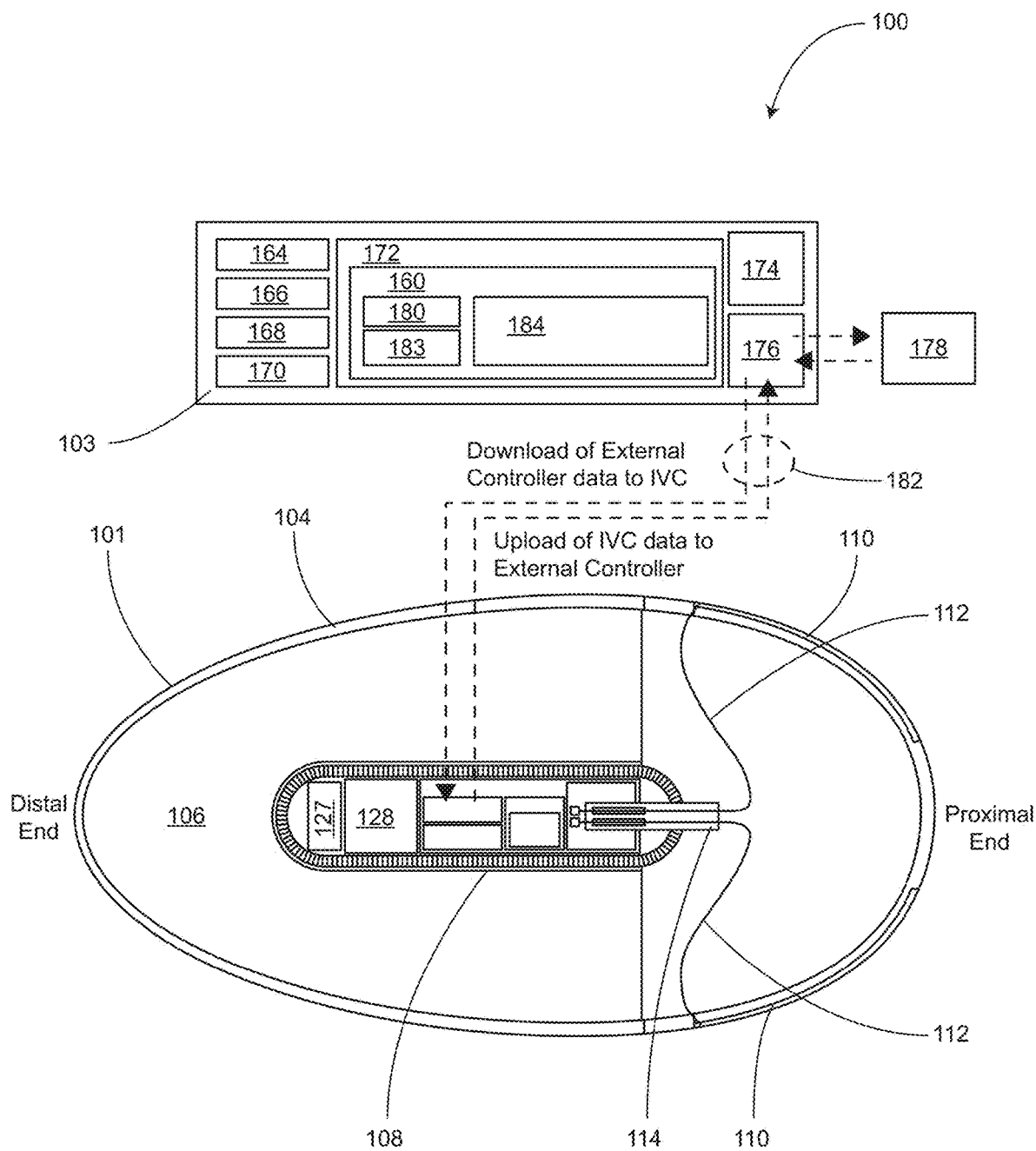
FIG. 24 shows a high-level block diagram, illustrating by way of example, both the intravaginal components and the external controller in an IVES device configured to operate in accordance with embodiments of the present invention.

An exemplary embodiment of an IVES device 100 constructed in accordance with the present invention will now be presented and discussed in more detail, starting first with a more detailed discussion of the set of intravaginal components 101 (illustrated in FIGS. 4 through 23), followed thereafter with a more detailed discussion of the external controller 103 (illustrated in FIGS. 24 through 29). Notably, the best illustration of the entire IVES device 100, including both the set of intravaginal components 101 and the external controller 103, is illustrated in FIG. 24, which is also discussed in more detail below.

For purposes of the discussion that follows, "proximal" means nearer to the central portion of the body and distal means farther from the central portion of the body. The proximal portion of the vagina is the innermost and uppermost portion of the vagina near the uterine cervix. The distal portion of the vagina is the lowermost portion of the vagina near the vaginal orifice. Anterior means toward the front of the body and posterior means toward the back of the body. Medial means at, near or approaching the vertical midline of the body, when viewed from the front or rear, and lateral means at some distance away from the vertical midline of the body, as in at, near or approaching the sides of the body, when viewed from the front or rear.

Figure 4:
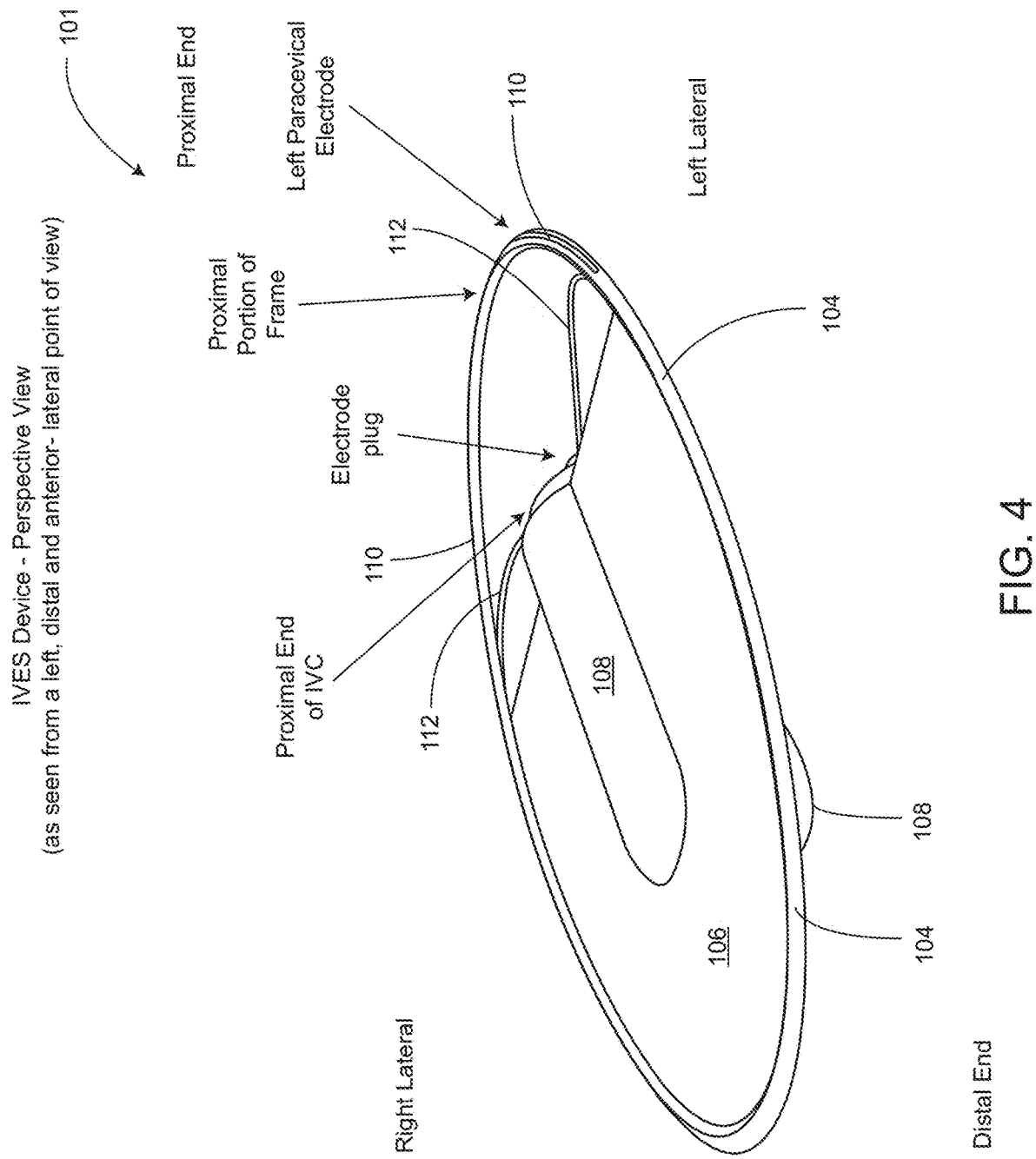
FIG. 4 shows a perspective view of some of the intravaginal components of an exemplary IVES device constructed in accordance with one embodiment of the present invention as seen from a left, distal and anterior-lateral point of view.
Figure 5:
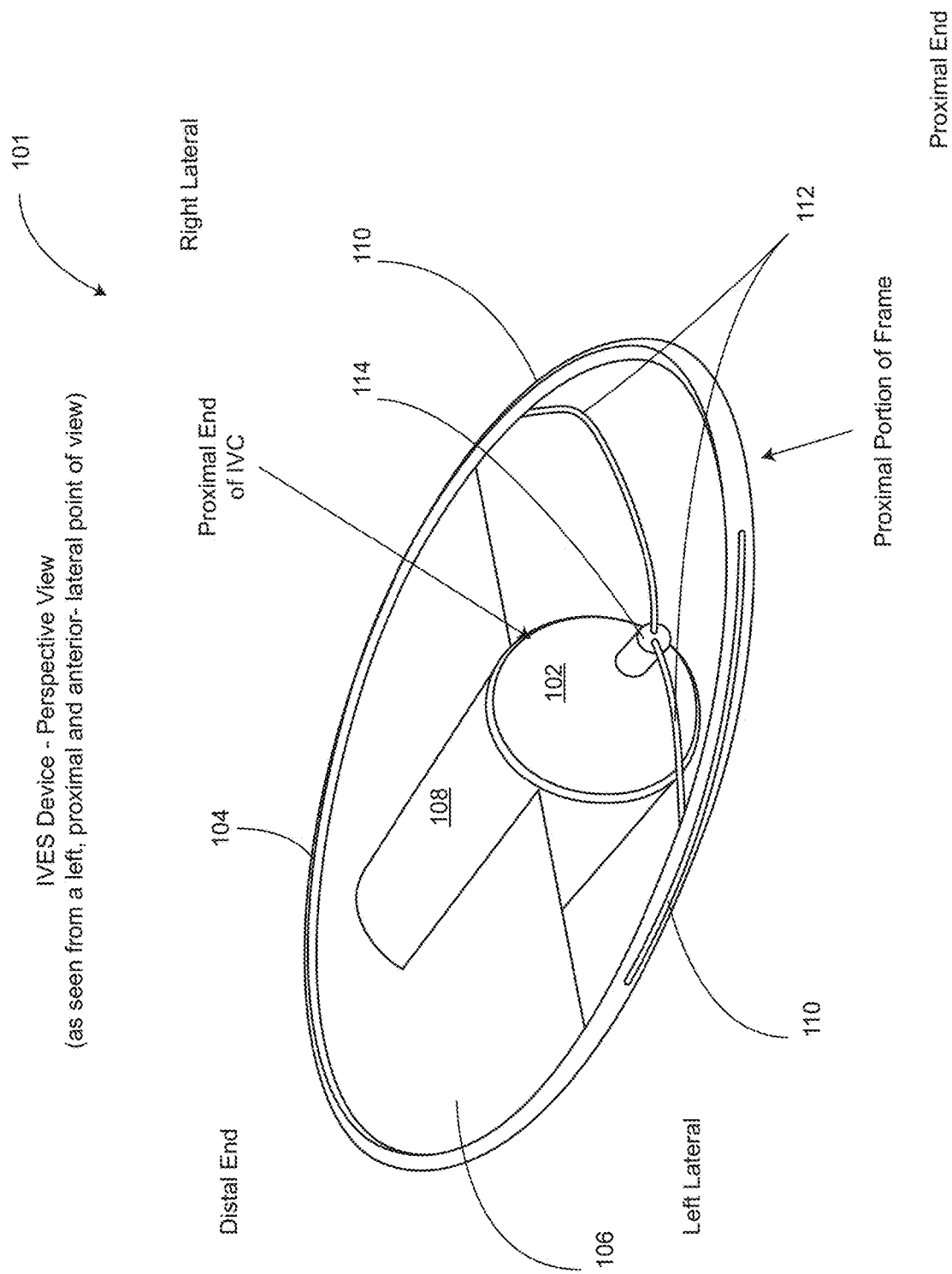
FIG. 5 shows a perspective view of some of the intravaginal components of the IVES device as seen from a left, proximal and anterior-lateral point of view.
Figure 6:
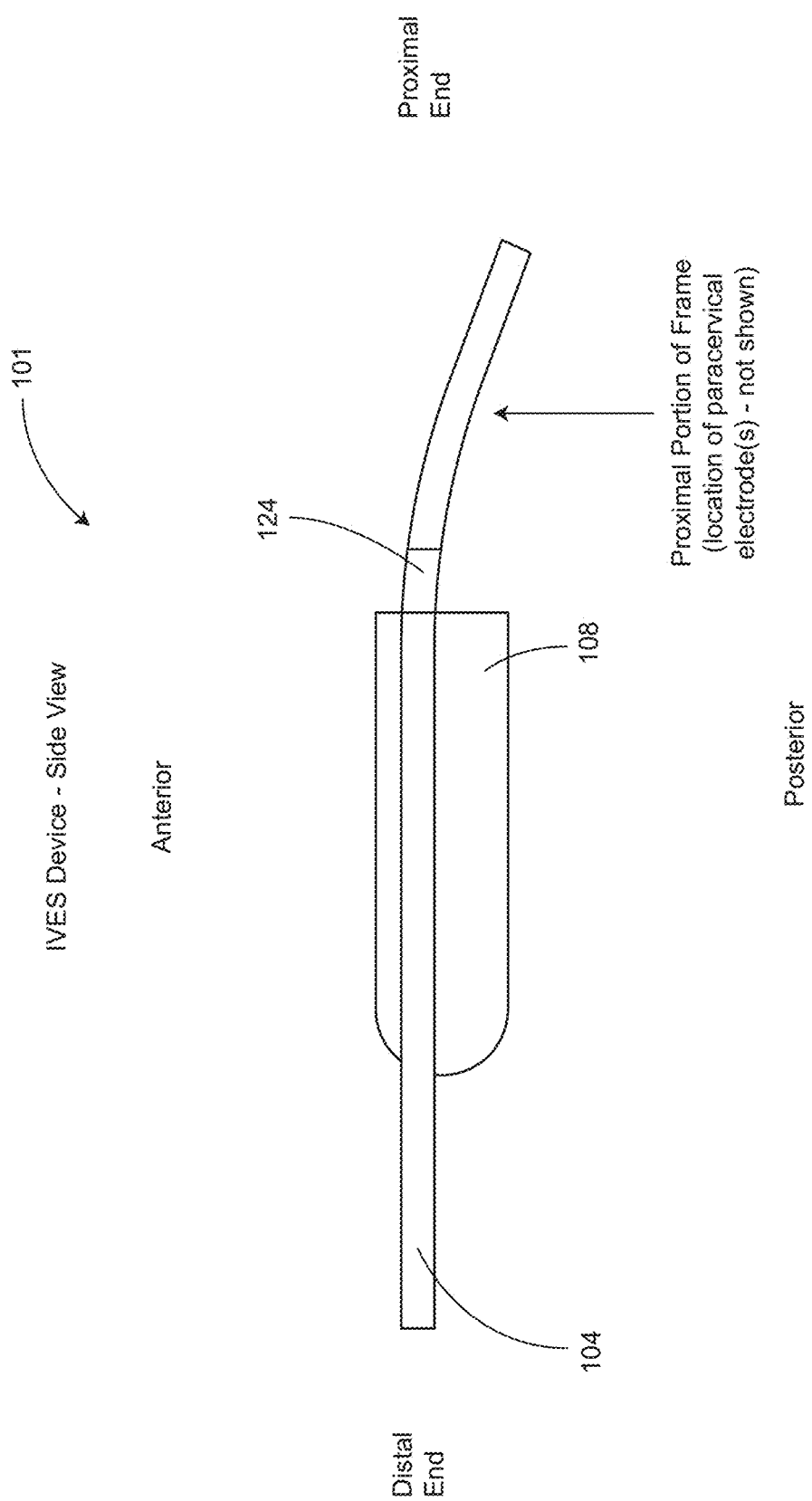
FIGS. 6, 7, 8, and 9 show a side view, a top view, a transverse cross-section view (viewed from the distal end of some of the intravaginal components of the IVES device), and a longitudinal cross-section view, respectively.
Figure 7:
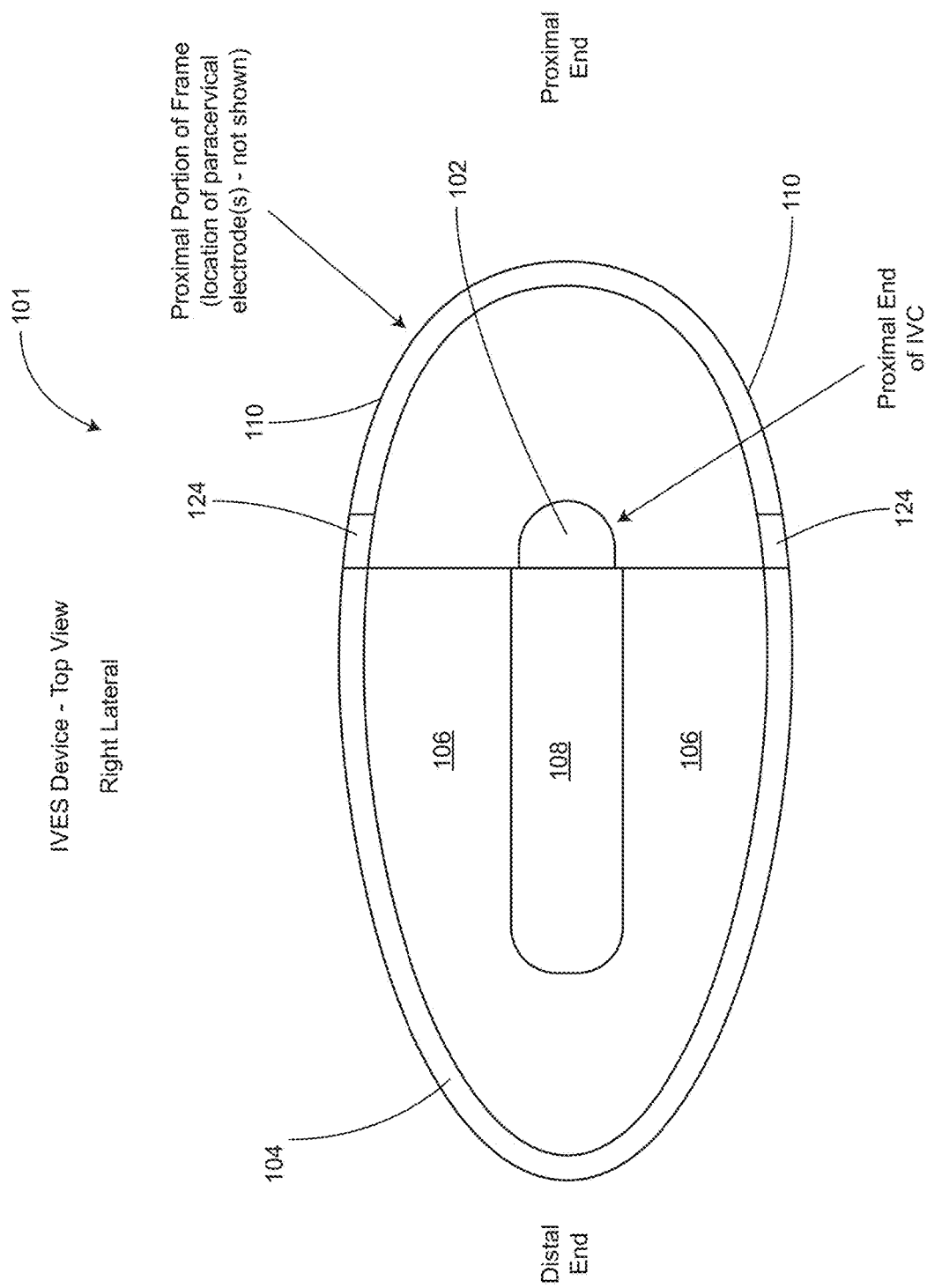
Figure 8:
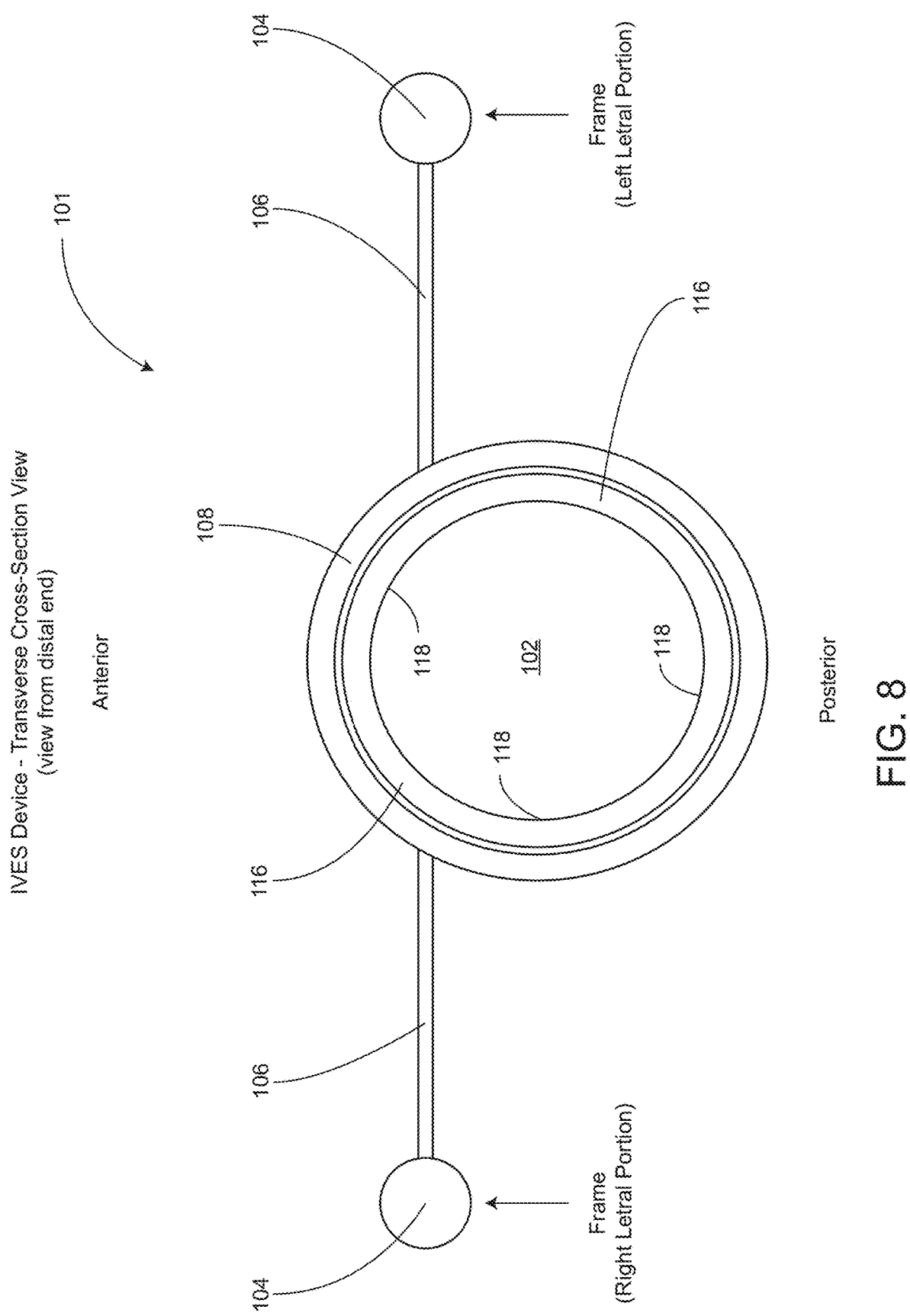
Figure 9:
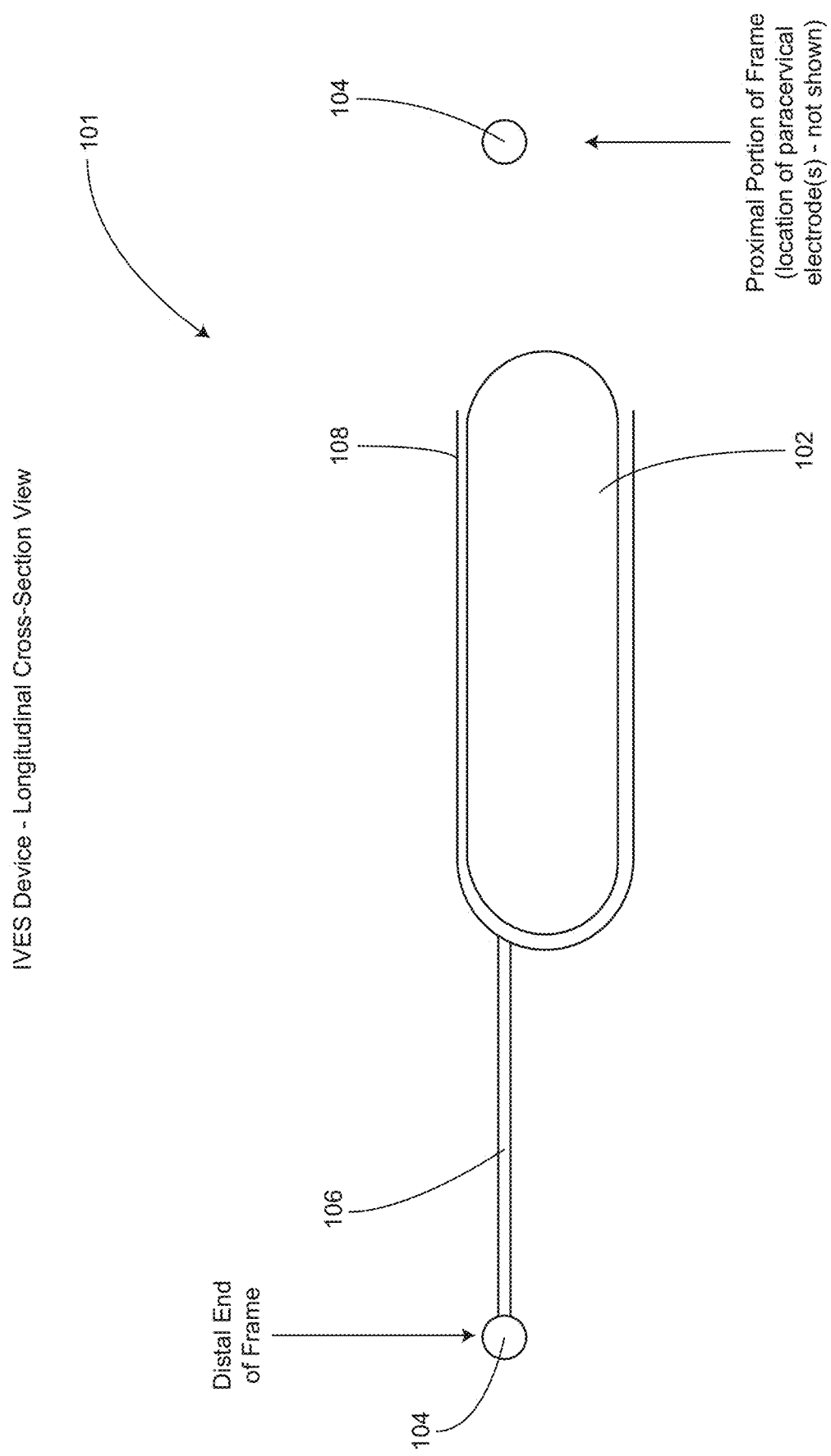

FIG. 4 shows a perspective view of the set of intravaginal components 101 for one embodiment of an IVES device 100 constructed in accordance with one embodiment of the present invention, as the set of intravaginal components 101 would appear if observed from a left, distal and anterior-lateral point of view. FIG. 5 shows a perspective view of the set of intravaginal components 101 as it would appear if observed from a left, proximal and anterior-lateral point of view. FIGS. 6, 7, 8, and 9 show a side view, a top view, a transverse cross-sectional view (viewed from the distal end of the set of intravaginal components 101), and a longitudinal cross-section view, respectively. As shown in FIGS. 4, 5, 6, 7, 8 and 9, the set of intravaginal components 101 generally comprises an intravaginal capsule (IVC) 102, a frame 104, a sling 106, an IVC pouch 108, one or more pairs of paracervical electrodes 110, connecting wires 112 and an electrode plug 114.

The Frame

The frame 104 is a structural element that is designed to reside comfortably in a woman's vagina when the set of the intravaginal components 101 is in use. Its core may be made of a semirigid, yet flexible material, such as a coiled spring made of metal or plastic, a rod made of metal, plastic or fiberglass, or a combination of several of these materials. In addition, the material or materials used in the frame 104 may have different configurations and properties in different areas of the frame 104 to achieve the semi-rigidity or flexibility desired for that area of the frame 104. Notably, those skilled in the art will recognize and appreciate that a variety of alternative construction materials may be suitably substituted for the aforementioned materials without departing from the scope of the present invention.

In one embodiment, the original shape of the frame 104 is substantially elliptical. However, it forms a posteriorly directed curvilinear shape when its lateral portions are compressed toward each other. The frame 104 is configured so that it has a propensity to return to its original shape when compressive forces are released. The compressive forces are introduced, for example, when the user squeezes the lateral portions of the frame 104 toward each other with the thumb and fingers of one hand prior to its insertion into the vagina. The compressive forces are reduced after the set of intravaginal components 101 passes entirely into the vagina 146 and the patient stops compressing together the lateral portions of the frame 104.

Suitably, the proximal and distal ends of the frame 104 are typically the most flexible portions of the frame 104, allowing significant compression of the frame 104 along its longitudinal axis. Compression of the frame 104 along its longitudinal axis and the resulting posterior curvature of the frame 104 make insertion of the intravaginal components 101 into the vagina easier to accomplish. Once the intravaginal components 101 are completely inserted into the vagina and the compression forces on the lateral portions of the frame 104 are removed, the frame 104 returns to its original configuration, at which point the distal end of the frame 104 rests upon the anterior vaginal wall behind the synthesis pubis and the proximal end of the frame 104 rests upon the vaginal epithelium in the posterior vaginal fornix (refer to FIG. 12, discussed in more detail below). In this configuration inside the vagina, the paracervical electrodes 110 embedded in the surface of the covering of the proximal portion of the frame 104, will come into contact with the vaginal epithelium in the lateral vaginal fornices. The lateral portions of the frame 104 are configured to gently press against the lateral walls of the vagina, keeping the frame 104 and the rest of the intravaginal components 101 of the IVES device 100 in the proper position within the vagina.

In another embodiment of the present invention, a "transitional" portion 124 (shown best in FIGS. 6 and 7) may be located in both of the lateral portions of the frame 104 between the point where the attachment of the sling 106 to the lateral portions of the frame 104 terminates and the distal end of paracervical electrodes 110 embedded in the covering of the proximal portion of the frame 104. The transitional portion 124 of the frame 104 may be curved slightly posteriorly and may be more flexible than the other portions of the frame 104 to facilitate the positioning of the proximal portion of the frame 104 in the posterior and lateral vaginal fornices when the intravaginal components 101 are introduced into the vagina. The propensity of the transitional portion 124 of the frame 104 to return to its original configuration after any pressure applied to it is released will cause the proximal portion of the frame 104 to apply gentle pressure superiorly and posteriorly to the vaginal epithelium in the posterior and lateral vaginally fornices, keeping the paracervical electrodes 110 in contact with the paracervical vaginal epithelium in the lateral fornices and properly positioned to deliver electrical stimulation to the pelvic and paracervical nerves.

The Sling and IVC Pouch

As shown best in FIGS. 4 through 8, the sling 106 is a thin membrane of a flexible, medical grade material, such as silicone rubber, for example, which is attached to the inner aspect of the distal and lateral portions of the frame 104. The IVC pouch 108 is a cylindrically shaped pouch, bag, sack or pocket in the sling 106 that is suitably aligned longitudinally with the midline of the set of intravaginal components 101. The IVC pouch 108, which is typically made from the same medical grade material used to make the sling 106, has a closed end distally and an open end proximally. The open end of the IVC pouch 108 is aligned with the proximal edge of the sling 106. Notably, those skilled in the art will recognize and appreciate that a variety of alternative construction materials may be suitably substituted for the aforementioned silicone rubber in the sling 106, the IVC pouch 108 and the covering of the frame 104 without departing from the scope of the present invention.

The Intravaginal Capsule

Figure 14:
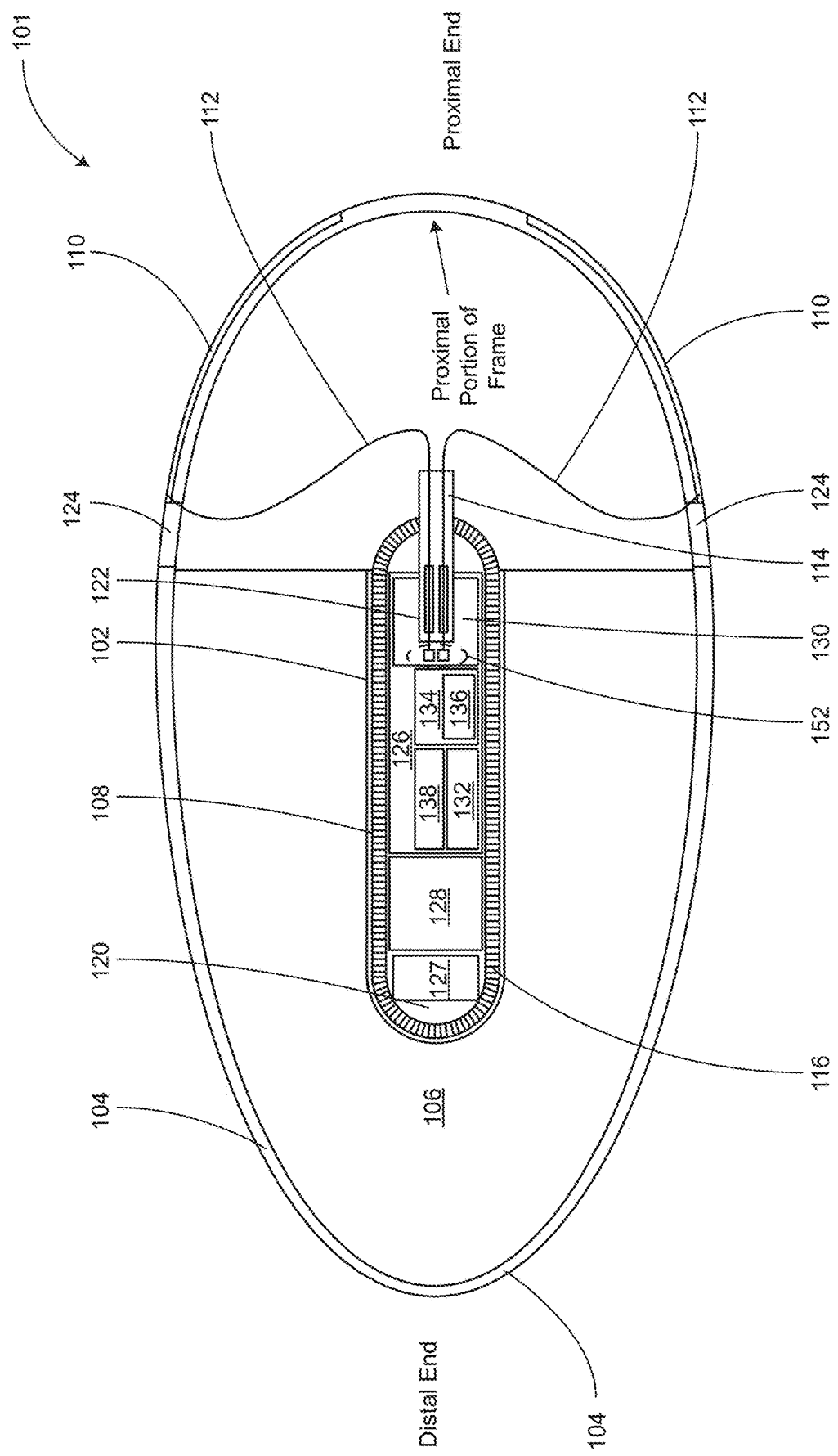
FIG. 14 shows a more detailed view of the primary intravaginal components of one embodiment of the IVES device.

As shown best in FIG. 14, the IVC 102 typically comprises a hard-plastic cylindrical shell 116 with rounded ends, and the shell 116 has interior walls 118 that define an interior cavity 120 for housing most of the electronic parts of the intravaginal components 101. The electronic components inside the shell 116 of the IVC 102 may include, for example, a printed circuit board 126, a rechargeable battery 128, an inductive charging coil 127 for charging the rechargeable battery 128, an electrical stimulation generator 130, a microprocessor 132, a memory 134, a local control program 136 in the memory 134, and a radio frequency transceiver 138. These electronic components are discussed in more detail below with references to FIG. 14.

Notably, although the IVC 102 of the exemplary embodiments described herein and shown in the accompanying figures has a longitudinal cross section that is cylindrical and a transverse cross section that is round, it will be understood that in other embodiments, the shape of the IVC 102 may be different. It should also be understood that the frame 104 may be manufactured in several different sizes and with materials that allow modifications to the manufactured shape so that they can be "custom fit" for individual users having a variety of different body sizes, body shapes and body conditions.

Figure 10A:
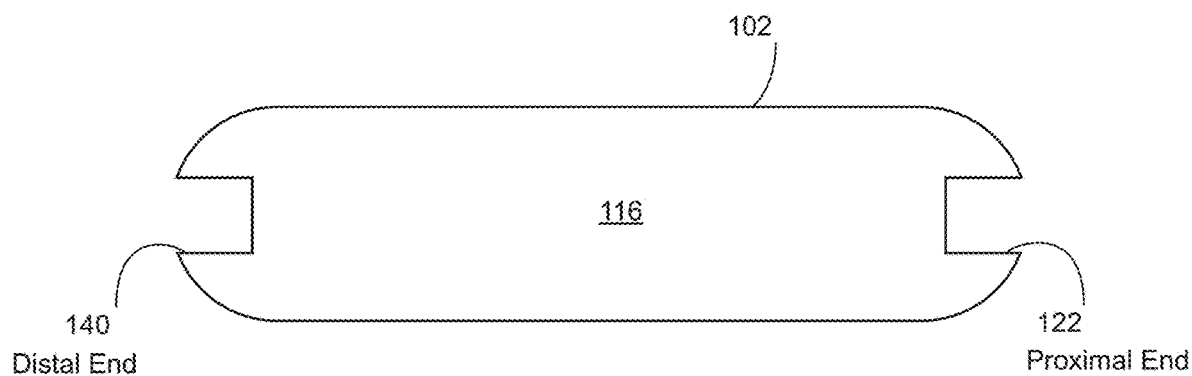
FIGS. 10A, 10B and 10C show, respectively, an orthogonal view of the IVC, a distal end on view of the IVC, and a proximal end on view of the IVC.
Figure 10B:
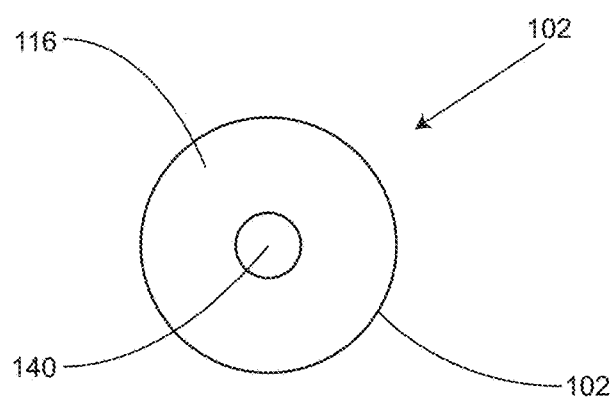
Figure 10C:
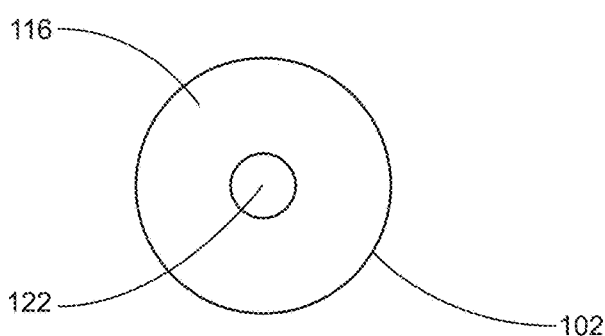

FIGS. 10A, 10B and 10C show, respectively, an orthogonal view of the IVC 102, a distal end on view of the IVC 102, and a proximal end on view of the IVC 102. The IVC 102 comprises a hard-plastic cylindrical shell 116 with rounded ends. The IVC shell 116 may (or may not) be permanently sealed to protect its contents from moisture and so that it cannot be opened by the user. As shown best in FIG. 10B, molded into the distal end of the shell 116 of the IVC 102 is an alignment pin receiving location 140 configured to receive the tip of an alignment pin (not shown) on an external wireless battery charger (also not shown in the figures). This alignment pin receiving location 140 facilitates proper alignment of the inductive charging coil 127 for the rechargeable battery 128 inside the IVC 102 and the charging coil of the external wireless battery charger. As shown best in FIG. 10C, molded into the proximal end of the shell 116 of the IVC 102 is a IVC socket 122, which is configured to receive an electrode plug 114 (described in more detail below). Optionally, heating elements may be embedded in the walls 118 of the cylindrical shell 116 of the IVC 102. Operating under the control of the external controller 103 and the IVES app 160 running on the external controller 103, these optional heating elements may be activated by the user via the external controller 103 to provide heat therapy for additional pain relief.

Figure 11:
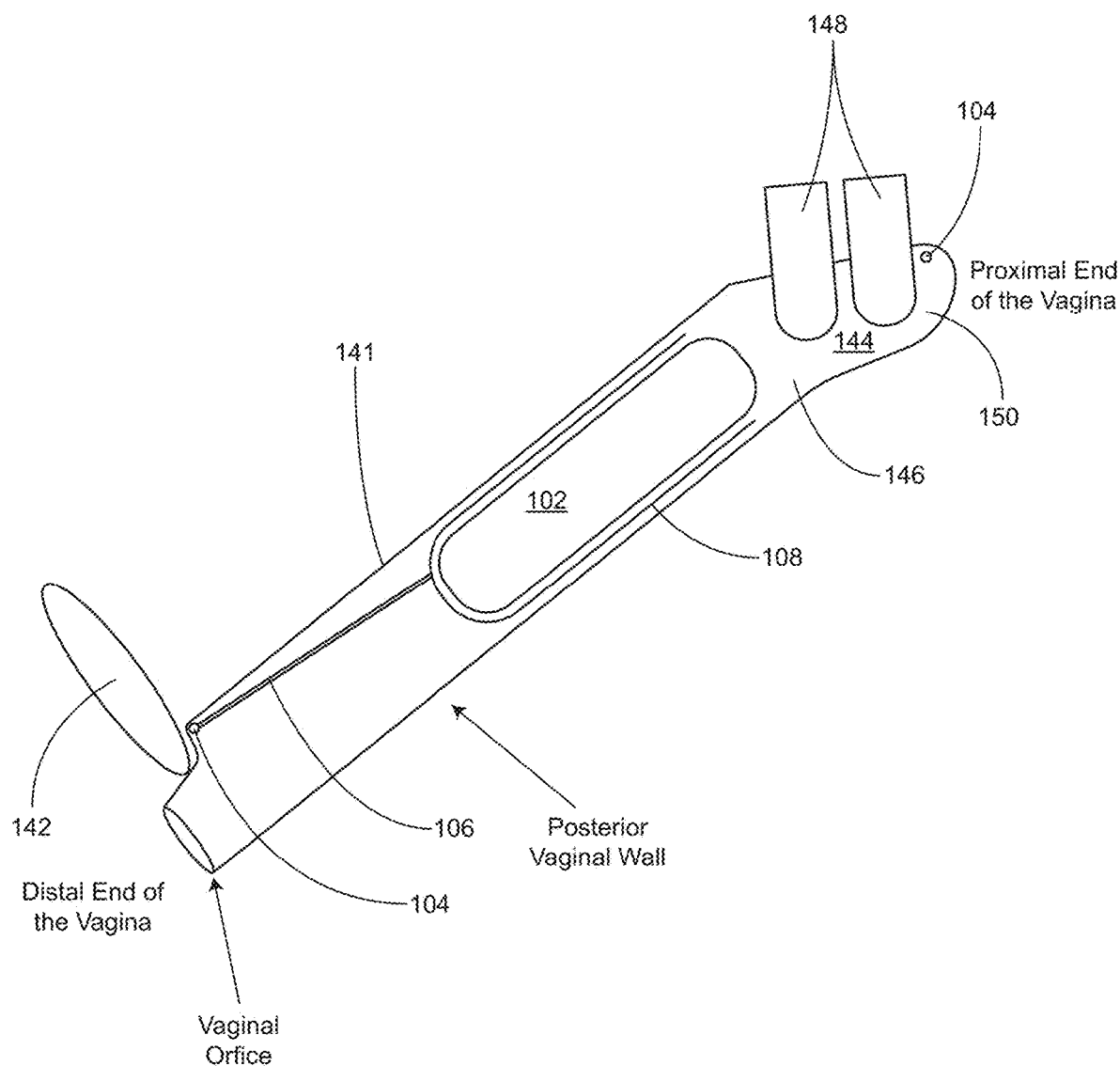
FIGS. 11, 12, and 13A show schematic diagrams illustrating the typical placement and orientation of the intravaginal components of an IVES device within the vagina in accordance with some embodiments of the present invention.
Figure 12:
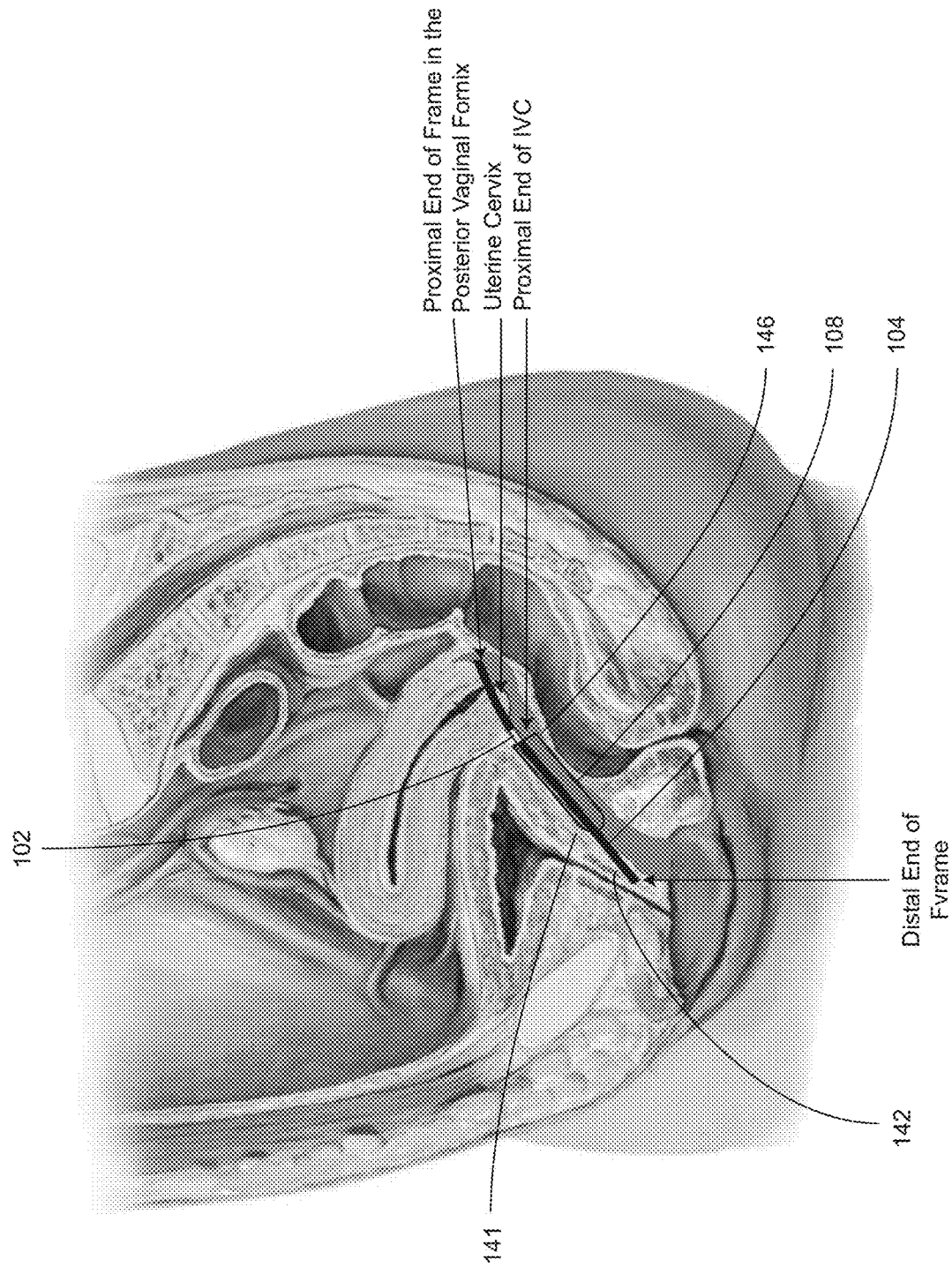
Figure 13A:
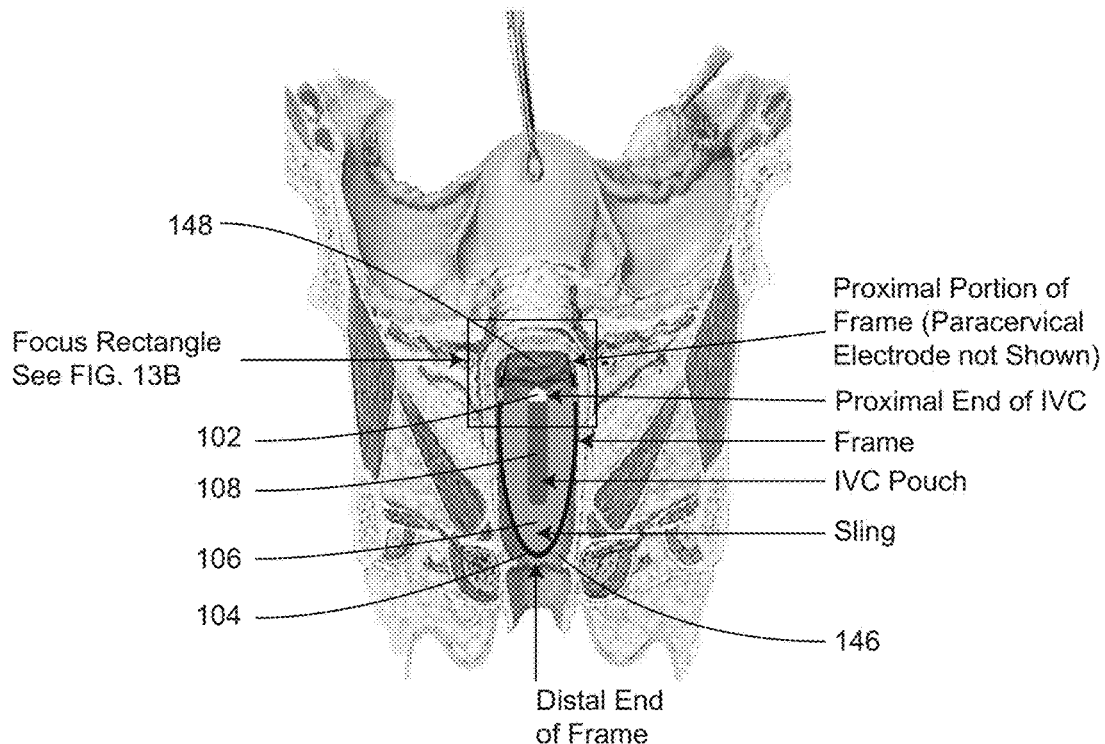

FIGS. 11, 12, and 13A show schematic diagrams illustrating the typical placement and orientation of the intravaginal components 101 of the IVES device 100 within the vagina in accordance with some embodiments of the present invention. As shown best in FIGS. 11 and 12, the distal end of the frame 104 rests against the anterior vaginal wall 141 behind the symphysis pubis 142. The proximal end of the frame 104 rests against the vaginal epithelium in the posterior vaginal fornix. The proximal portion of the frame 104 and the paracervical electrodes 110 residing thereon rests in the lateral vaginal fornices 144. And the lateral portions of the frame 104 press gently on the lateral walls of the vagina 146 to help keep the intravaginal components 101 of the IVES device 100 in the proper position within the vagina 146. When the intravaginal components 101 of the IVES device 100 are in the proper position inside the vagina 146, the IVC 102 will sit substantially in the middle portion of the vagina 146 and have a longitudinal orientation.

Figure 13B:
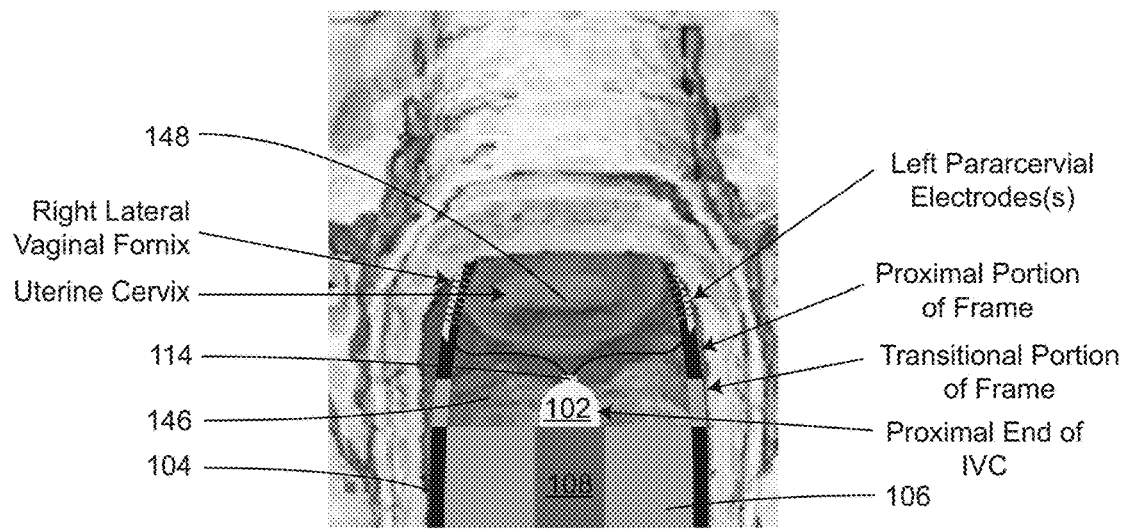
FIG. 13B shows an enlarged view of the upper vagina and uterine cervix with the proximal end of the set of intravaginal components of IVES device in-situ to illustrate the proper positioning of the paracervical electrodes in the lateral vaginal fornices.

FIG. 13A shows an anterior transverse sectional view of the female pelvis with the intravaginal components 101 in-situ within the vagina 146. FIG. 13B shows an enlarged view of the portion of FIG. 13A enclosed by the focus rectangle drawn over the upper vagina 146 and uterine cervix 148 in FIG. 13A. The upper vagina 144 and uterine cervix 148 with the proximal end of the intravaginal components 101 in-situ to illustrate the proper positioning of the paracervical electrodes 110 in the lateral vaginal fornices 144.

Embodiments of the present invention may be manufactured in a variety of different sizes, and have a variety of longitudinal lengths for the frame 104 (for example from 6.5 to 8.5 centimeters, in increments of 5 millimeters) in order to accommodate the various vaginal depths of the women who may use the IVES device 100. The lateral flexibility of the frame 104 increases the IVES device 100's ability to address and accommodate differences in vaginal caliber among different women. The increased flexibility of the transitional portion 124 of the frame 104 and its propensity to return to its original configuration, when pressure placed upon it is released helps maintain the proper positioning of the paracervical electrodes 110 in the lateral vaginal fornices 144. The malleable sling 106 allows the intravaginal components 101 of the IVES device 100 to accommodate the overall shape of the vagina 146 for the women who may use the IVES device 100.

FIG. 14 shows a more detailed view of the intravaginal components 101 in an embodiment of the IVES device 100, including the frame 104, the sling 106, the IVC pouch 108, the IVC 102, the IVC socket 122 in the IVC 102 (which is configured to receive the electrode plug 114). The intravaginal components 101 also include one or more pairs of electrode units 152. As shown in FIGS. 14 through 18, the shell 116 of the IVC 102 comprises a hollow space defining an internal cavity 120 that houses a number of electronic components, including the rechargeable battery 128, the inductive charging coil 127 that can be energized by placing it within range of an operating external inductive charger (not shown in the figures), a printed circuit board 126 and an electrical stimulation generator 130. The printed circuit board 126 carries a radio frequency transceiver 138, a microprocessor 132, a memory 134, a local control program 136 in the memory 130 and an electrical stimulation generator 130.

The printed circuit board 126 is typically affixed to an interior wall 118 of the shell 116. The rechargeable battery 127, electrical stimulation generator 130, microprocessor 132, memory 134, local control program 136 and radio frequency transceiver 138 are all attached to the printed circuit board 126 to form an electrical circuit. The local control program 136 stored in the memory 130 comprises one or more programming modules having programming instructions that, when executed by the microprocessor 132, will cause the microprocessor 132 to perform certain functions herein described, including sending electronic signals to the electrical stimulation generator 130, and thereby control the output of the electrical stimulation generator 132. The characteristics (or profile) of the electrical stimulation produced by the electrical stimulation generator 130 may be varied by using, for example, constant current versus constant voltage, low frequency versus high frequency stimulation, tonic stimulation versus burst stimulation and by altering the pulse width, frequency and amplitude of the electrical stimulation being produced.

The radio frequency transceiver 138, operating under the control of the microprocessor 132 and the local control program 136, establishes a wireless data communications channel (typically using Bluetooth®, or some other near field communication protocol) with an application program (the "IVES remote control application or IVES app") 160 running on an external data communications device (the "external controller"), such as a smart phone, tablet computer or personal computer. The radio frequency transceiver uses the established wireless communication channel to receive data comprising operating instructions and other parameters for the IVES device 100 from the IVES app 160 on the external controller. The radio frequency transceiver 138 sends these incoming data, operating instructions and other parameters to the microprocessor, which executes programming instructions in the local control program 136 stored in the memory 130 to cause the electrical stimulation generator 136 to generate and send to the paracervical electrodes 110 electrical stimulations to stimulate the pelvic and paracervical nerves in accordance with the instructions and parameters received from the IVES app 160 operating on the external controller 103 (which is discussed in more detail below). In preferred embodiments, the components of the IVC 102 can be configured to receive operating instructions and parameters over the wireless communications channel both before and after intravaginal components are placed inside the vagina 146. Suitably, the radio frequency transceiver 138 connected to the printed circuit board 126 of the IVC 102 may also be used to transmit status information (e.g., remaining battery charge) to the IVES app 160.

The electrical stimulation generator 130 operates under the control of the microprocessor 132 and the local control program 136, which tells the electrical stimulation generator 130 how to convert the DC current from the battery 128 into the appropriate electrical stimulation patterns ("ESP's") to be delivered to the pelvic and paracervical nerves by way of the one or more electrical stimulation circuits, which are each comprised of a pair of related electrode units 152. Suitably, one of the paracervical electrodes 110 is the positive pole of the circuit, and the other paracervical electrode is the negative pole of the circuit. Preferably, a variety of different ESP's may be created, saved, recalled and activated by the patient by manipulating controls in the user interface of the IVES application program running on the external controller. Some of the features implemented in the user interface of the IVES application program 160 are discussed in more detail below.

The memory 130 on the printed circuit board 126 stores the programming instructions that comprise the local control program 136. When executed by the microprocessor 130, the programming instructions will cause the microprocessor 132 to carry out the steps of one or more predefined algorithms. These algorithms are typically executed in response to operating instructions and parameters input by the user via the user interface of the IVES app 160 running on the external controller 103. For example, the algorithms are typically arranged to allow the user to select and adjust the electrical stimulation patterns (ESP's) output by the electrical stimulation generator 130 in accordance with either pre-installed ESP's, or ESP's created by the user via the user interface. Preferably, the memory 134 also stores historical data regarding the operations and performance of the IVES device 100, which is periodically uploaded to the external controller 103 via the radio frequency transceiver 138 on the printed circuit board 126 of the IVC 102. Preferably, but not necessarily, IVES App 150 on the external controller 103 further includes program instructions that, when executed by the microprocessor 132, will cause the microprocessor 132 to use the radio frequency transceiver 126 in the external controller to wirelessly transmit historical data uploaded to the external controller 103 to other computing devices and made available to the patient's practitioner and/or others to improve the use of the IVES device 100 by the patient and others. The memory 134 may also store programming instructions that, when executed by the microprocessor, will cause the microprocessor to run a self-diagnostic test prior to sending electrical stimulation signals to the paracervical electrodes 110, and automatically generate a message for the user and then turn off the IVES device 100 should a fault be detected during the self-diagnostic test.

The Electrode Plug

Figure 15:
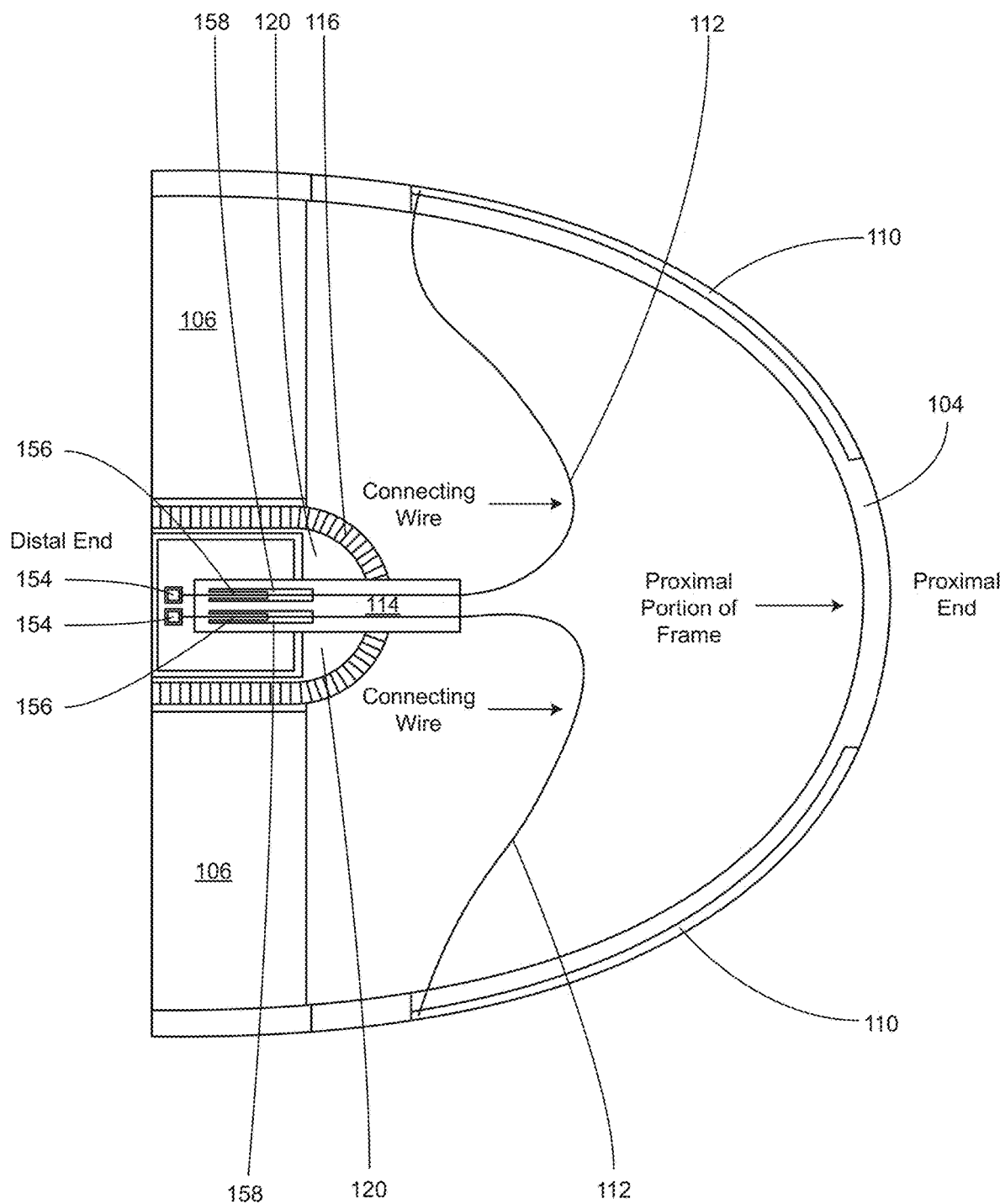
FIG. 15 shows the components of an embodiment of the IVES device with a single electrical stimulation circuit comprised of a pair of electrode units, which are used create a single electrical field with one paracervical electrode being the positive pole of the circuit and the other paracervical electrode being the negative pole of the circuit.
Figure 16:
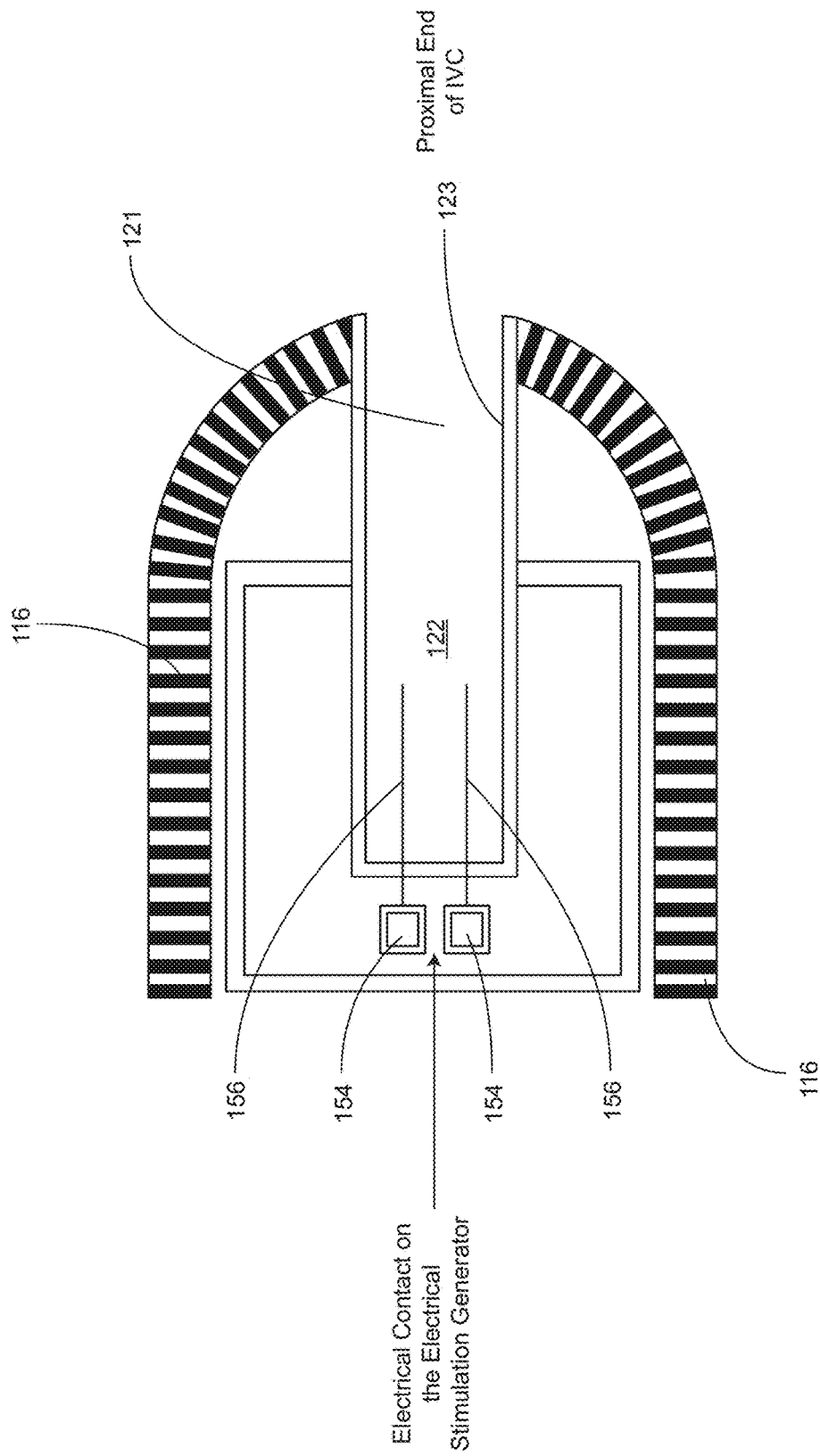
FIG. 16 shows a detailed cross-sectional view of the IVC socket in the proximal end of the IVC 102 without the electrode plug inserted into the IVC socket.

The electrode plug 114 is suitably configured to be removably connected to the IVC 102 by insertion into the IVC socket 122 (shown best in FIGS. 14, 15 and 16). The electrode plug 114 is comprised of a plug (see FIG. 17) made from a semi-firm compressible medical grade material surrounding one or more pairs of female electrical contacts configured to receive corresponding male electrical contacts at the distal end of the IVC socket 122 whenever the electrode plug 114 is inserted into the IVC socket 122. In some embodiments, the electrode plug 114 may have a slightly larger cross-section than the cross-sectional dimensions of the IVC socket 122. In such embodiments, the propensity of semi-firm compressible material used to make the plug to return to its original shape once compressive forces place upon it are released make the connection between the IVC socket 122 and the plug substantially moisture proof. In other embodiments, the electrode plug 114, the IVC socket 122, or both, may have detents holding O-rings to provide moisture protection for the electrical contacts or other elements of the plug 114 and/or IVC socket 122. The shape of the perimeter walls of the electrode plug 114 and IVC socket 122 are designed so that corresponding male contacts at the distal portion of the IVC socket 122 and female contacts in the plug are in alignment when the electrode plug 114 is inserted into the IVC socket 122. The electrode plug 114 may be removed from the IVC socket 122 in the IVC 102 and the IVC 102 may be removed from the IVC pouch 108 in order to completely separate the IVC 102 from the other components of the IVES device 100 for cleaning or replacement and to place the IVC 102 on the charging station to charge the battery in the IVC 102, for instance. It should be appreciated by one skilled in the art that, in an alternative embodiment, the male electrical contacts could be located in the electrode plug 114 and the female electrical contacts could be located in the IVC socket 122.

The Electrode Units

The electrical stimulation produced by the electrical stimulation generator 130 is delivered to the pelvic and paracervical nerves by one or more pairs of electrode units 152. Each electrode unit 152 is comprised of an electrical contact 154 on the electrical stimulation generator 130, a male electrical contact 156 located in the base of the IVC socket 122 that is electrically coupled to the electrical contact 154 on the electrical stimulation generator 130, a female contact 158 in the electrode plug 114 that creates an electrical connection with a corresponding male contact 156 when the electrode plug 114 is installed in the IVC socket 122. A connecting wire 112 extends from each female contact 158 to a paracervical electrode 110. The electrical stimulation generating components inside the IVC 102 cooperate to deliver the electrical stimulation to the pelvic and paracervical nerves through one or more electrical fields created by the one or more pairs of electrode units 152. Typically, one electrode unit 152 connected to one paracervical electrode is the positive pole of an Electrical Stimulation Circuit (ESC) and the other electrode unit 156 in the pair is the negative pole in the ESC.

The connecting wire 112 comprises a flexible and insulated wire, capable of carrying electric current in a circuit, which extends from a female electrical contact in the electrode plug 114 to the beginning of a paracervical electrode 110. The paracervical electrode 110 comprises one or more wires, capable of conducting electrical current, which are embedded in the covering of the proximal portion of the frame 104. In one embodiment, the surface area of a paracervical electrode 110 may be increased by attaching a thin "wafer" of electrode material (that might be round, square or rectangular for example) to the paracervical electrode 110 wire or wires embedded in the covering of the proximal portion of the frame 104. The wire(s) and wafers comprising the paracervical electrode 110 are either not insulated or minimally insulated so the electrical stimulation generated by the electrical stimulation generator and transmitted to the paracervical electrodes 110 is delivered to the paracervical vaginally epithelium, and hence, the pelvic and paracervical nerves.

Notably, those skilled in the art will recognize and appreciate that a pair of electrode units 152 create an electrical field to deliver a specific electrical stimulation pattern to the pelvic and paracervical nerves and multiple pairs of electrode units 152 could be used to deliver multiple electrical stimulation patterns to the pelvic and paracervical nerves at the same time. Thus, the electronic signals sent to the electrical stimulation generator 130 by the microprocessor 132 operating under the control of the local control program 136 running in the memory 134 causes the electrical stimulation generator 130 to transmit one or more electrical stimulation patterns through one or more pairs of electrode units 152 causing neuromodulation of the pelvic and paracervical nerves. This neuromodulation of the pelvic and paracervical nerves reduces the pain associated with dysmenorrhea, dyspareunia and chronic pelvic pain.

Figure 17:
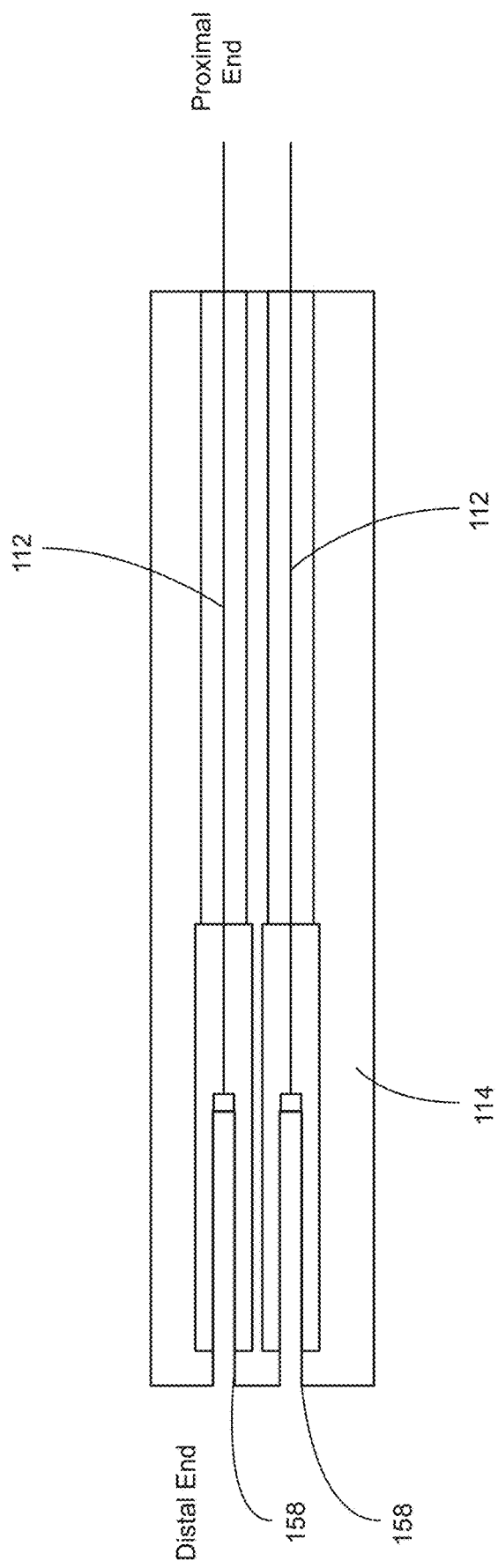
FIG. 17 shows a detailed cross-sectional view of the electrode plug surrounding a pair of female electrical contacts when the electrode plug has not been inserted into the IVC socket.
Figure 18:
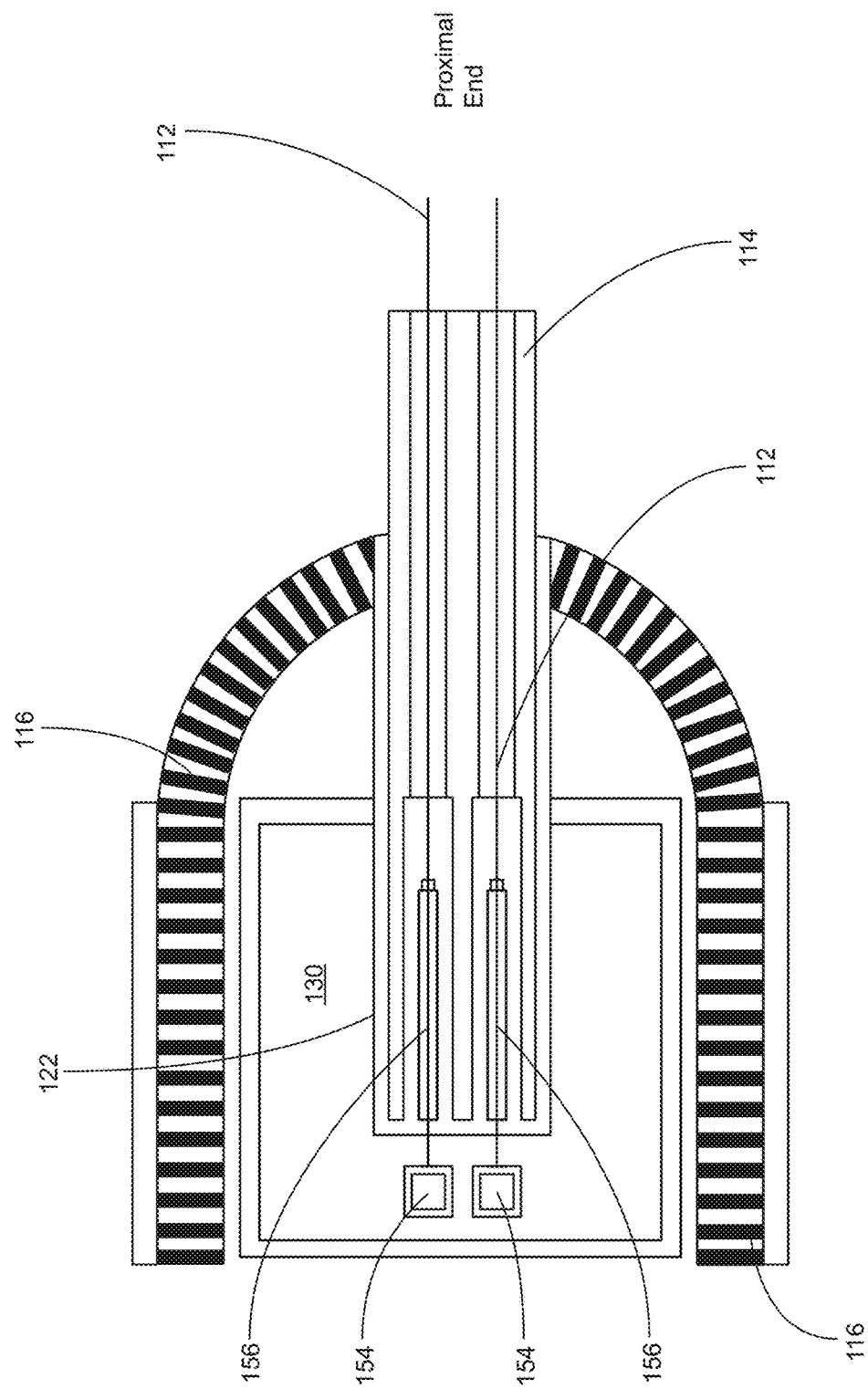
FIG. 18 shows a detailed cross-sectional view of the IVC socket with the electrode plug inserted into it in some embodiments of the present invention.

FIG. 15 shows the intravaginal components 101 of one embodiment of the IVES device 100, where there is a single electrical stimulation circuit comprised of a pair of electrode units 152, which are used create a single electrical field with one paracervical electrode 110 being the positive pole of the circuit and the other paracervical electrode being the negative pole of the circuit. FIG. 16 shows a detailed cross-sectional view of the IVC socket 122 in the proximal end of the IVC 102 without the electrode plug 114 inserted into the IVC socket 122. FIG. 17 shows a detailed cross-sectional view of the electrode plug 114 surrounding a pair of female electrical contacts when the electrode plug 114 has not been inserted into the IVC socket 122. FIG. 18 shows a detailed cross-sectional view of the IVC socket 122 with the electrode plug 114 inserted into it in some embodiments of the present invention.

As shown in FIGS. 16, 17 and 18, the IVC 102 has in its proximal end a IVC socket 122 configured to receive and removably hold the electrode plug 114. In some embodiments, the IVC socket 122 defines a cylindrical space 121 with the sidewalls 123 of the cylindrical space 121 and the base of the cylindrical space 121 at its distal end forming a physical barrier between the interior cavity 120 of the IVC 102 and the environment outside the IVC 102 to protect the printed circuit board 126 and other electronic components within the IVC 102 from moisture. In other embodiments, the sidewalls 123 of the IVC socket 122 may instead define a space having a different geometric shape, such as, for example, a half-cylinder shape, a rectangular solid or a triangular solid. In any case, the electrode plug 114 is suitably configured to have a size and shape that complements the inner space defined by the sidewalls 123 of the IVC socket 122 so as to enable easy insertion of the electrode plug 114 into the IVC socket 122, and is designed to create a moisture proof seal between it and the IVC socket 122. Located at the distal end of the IVC socket 122 are male electrical contacts 156 that are electrically coupled to electrical contacts 154 on the electrical stimulation generator 130 on the printed circuit board 126 inside the interior cavity 120 of the IVC shell 116. Built into the electrode plug 114 are female electrical contacts 158 configured to engage the male electrical contacts 156 at the distal end of the IVC socket 122.

As has been previously described, the paracervical electrodes 110 embedded in the surface of the covering of the proximal portion of the frame 104 are positioned so they will remain in contact with the paracervical vaginal epithelium of the lateral vaginal fornices while the IVES device 100 is in use. When the male electrical contacts 154 at the distal end of the IVC socket 122 in the IVC 102 are engaged with the female contacts 156 built into the electrode plug 114, and the IVES device 100 is switched on and operating, the electrical stimulations generated by the electrical stimulation generator 130 (operating under the control of the microprocessor 132 and local control program 136) are transmitted to the pelvic and paracervical nerves via an electrical stimulation circuit comprising at least one pair of electrode units 156.

Responding to instructions from the external comptroller 103 and under the control of the local control program 136 in the memory 134 of the IVC 102, the characteristics of the electrical stimulation produced by the electrical stimulation generator 130 may be varied by using, for example, constant current versus constant voltage, low frequency versus high frequency stimulation, tonic versus burst stimulation and by altering the pulse width, frequency and amplitude of the electrical stimulation being produced. Neuromodulation of the pelvic and paracervical nerves due to the electrical stimulation they receive will reduce or eliminate the pain associated with dysmenorrhea, dyspareunia and chronic pelvic pain originating in the uterus and other organs in the pelvis.

Figure 19A:
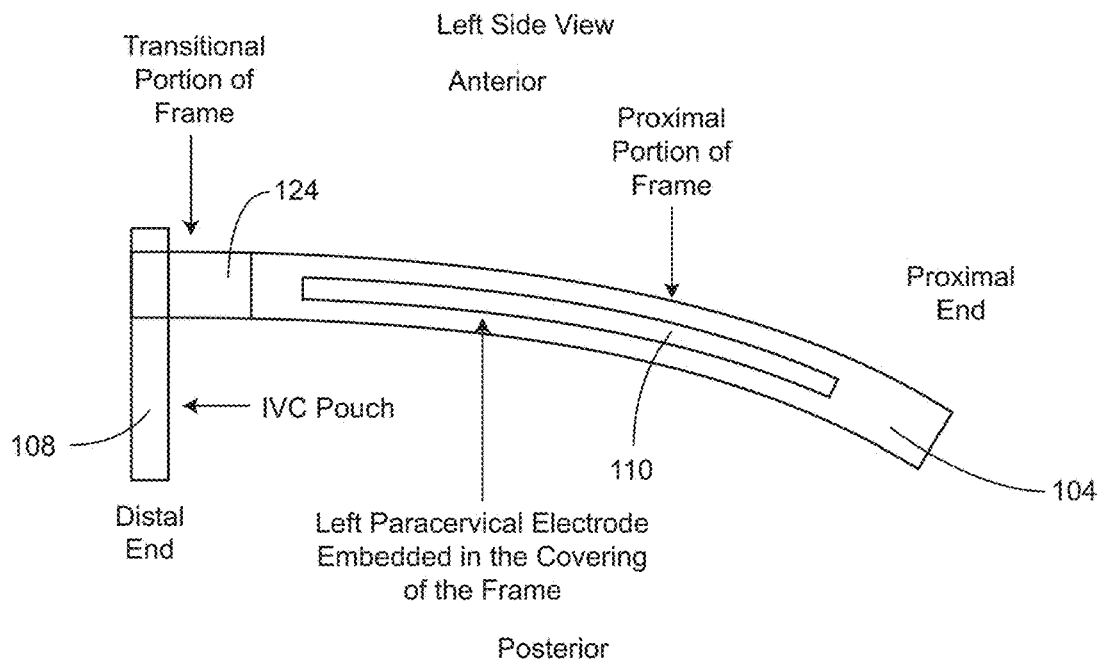
FIGS. 19A and 19B. shows the positioning of the paracervical electrodes embedded in the surface covering of the proximal portion of the frame in an embodiment of an IVES device, wherein one pair of electrode units are being used to create a single electrical stimulation circuit to produce a single electrical field between the paracervical electrodes.
Figure 19B:
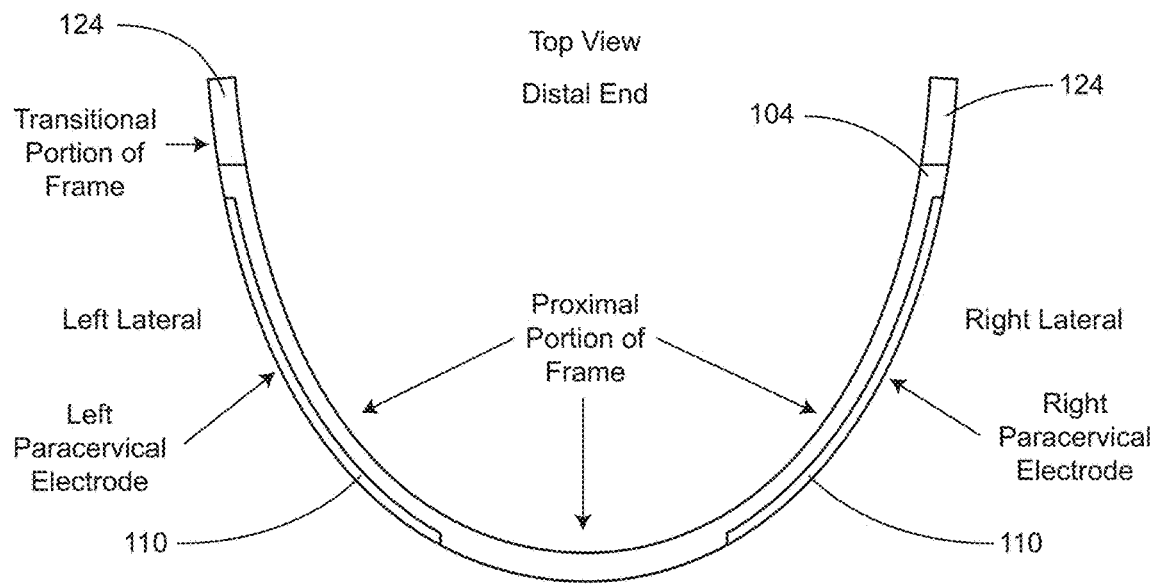

FIGS. 19A and 19B. show the positioning of the paracervical electrodes 110 embedded in the surface covering of the proximal portion of the frame 104 in an embodiment of the IVES device 100 where one pair of electrode units are being used to create a single electrical stimulation circuit to produce a single electrical field between the paracervical electrodes 110.

Figure 20:
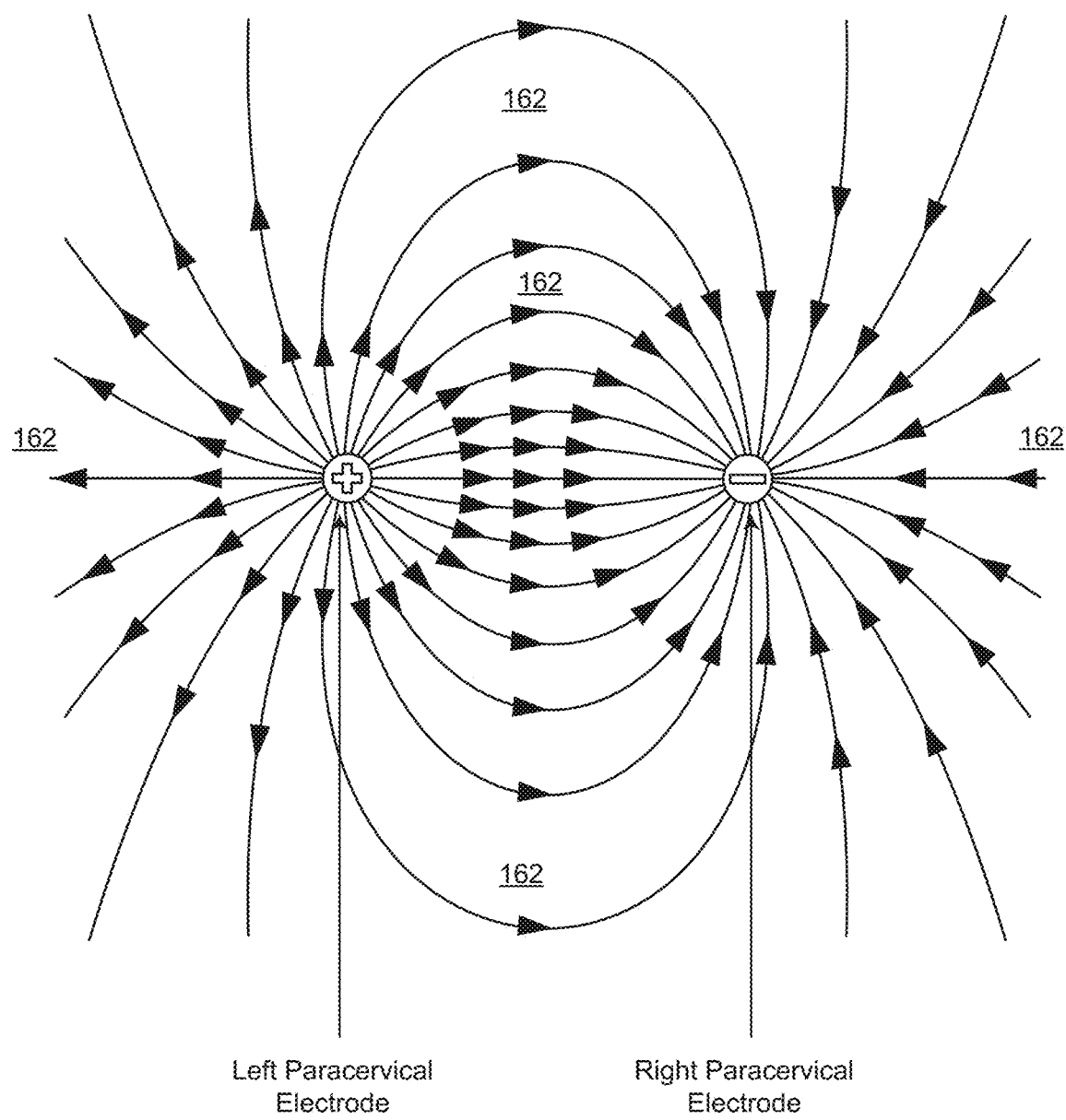
FIG. 20 shows a schematic representation of the electrical field generated by a single electrical stimulation circuit with a pair of paracervical electrodes positioned as shown in FIGS. 19A and 19B.

FIG. 20 shows a schematic representation of the electrical field 162 generated by a single electrical stimulation circuit with a pair of paracervical electrodes 110 positioned as shown in FIGS. 19A and 19B.

Figure 21A:
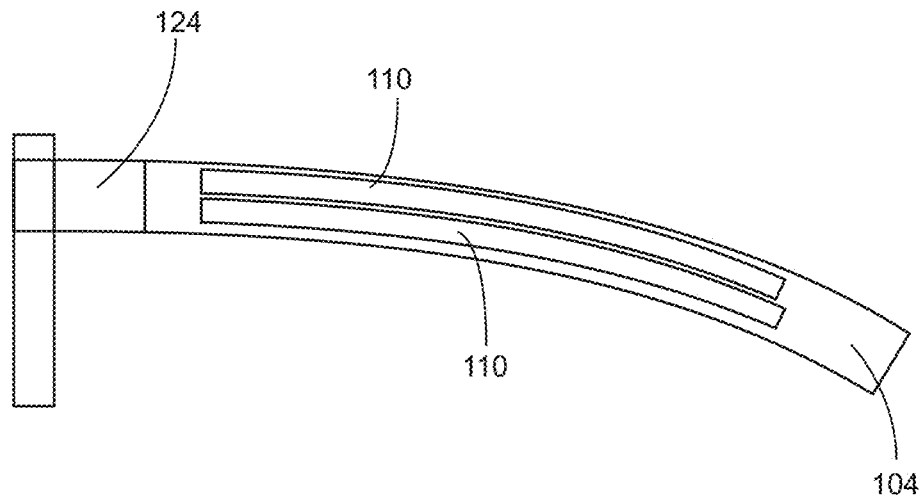
FIGS. 21A and 21B shows the positioning of two pairs of paracervical electrodes embedded in the surface covering of the proximal portion of the frame in an embodiment of the IVES device where two pairs of electrode units are used to create two electrical stimulation circuits.
Figure 21B:
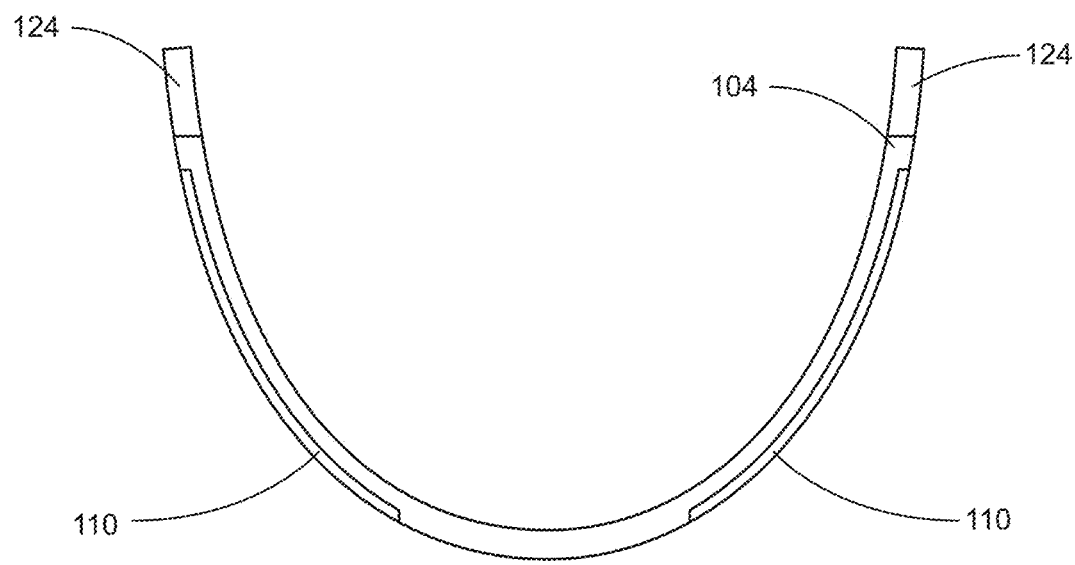

FIGS. 21A and 21B shows the positioning of two pairs of paracervical electrodes 110 embedded in the surface covering of the proximal portion of the frame 104 in an embodiment of the IVES device 100 where two pairs of electrode units are used to create two electrical stimulation circuits.

Figure 22:
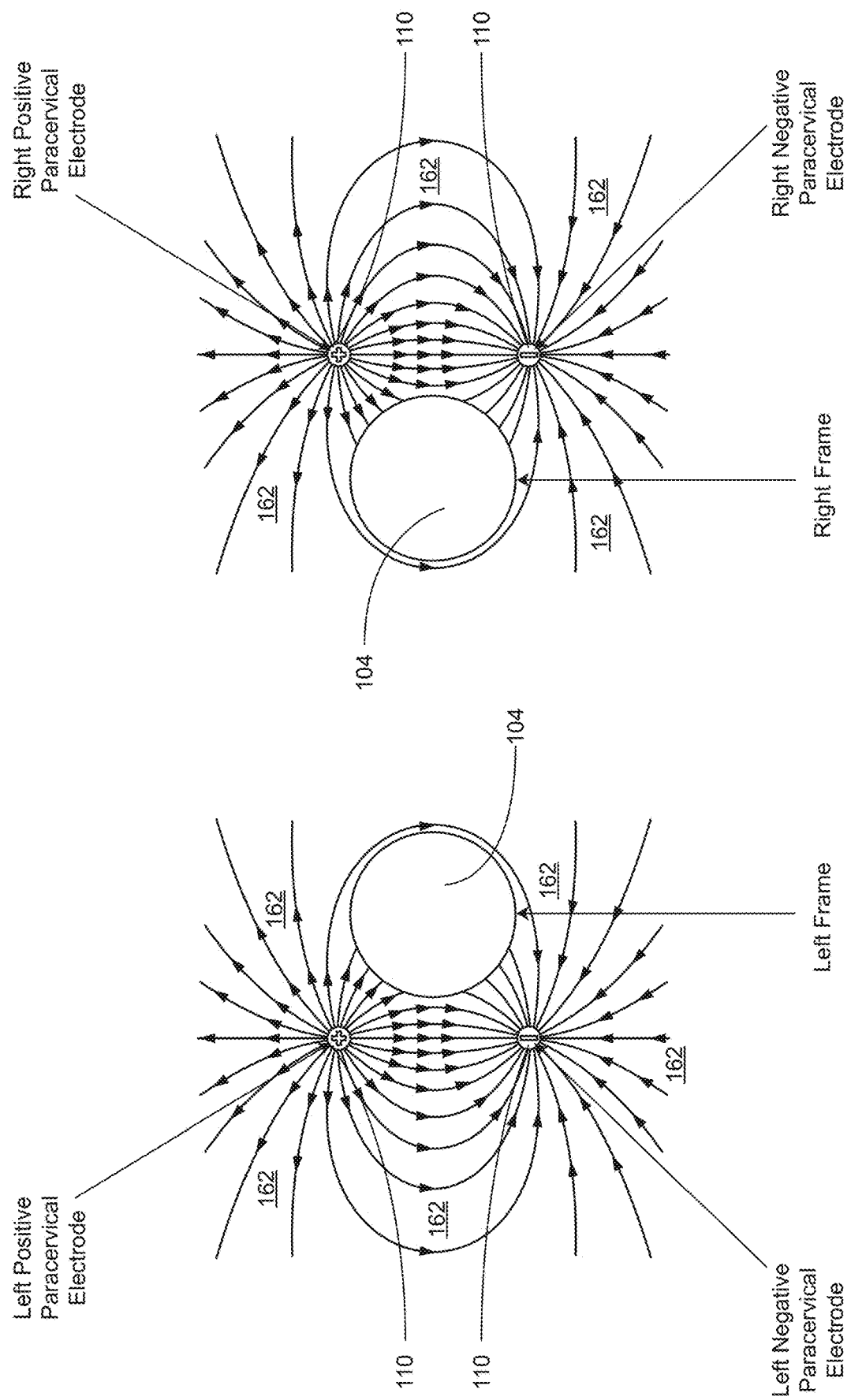
FIG. 22 shows a schematic representation of the electrical fields generated by two electrical stimulation circuits with two pairs of paracervical electrodes positioned as shown in FIGS. 21A and 21B if the positive electrode and the negative electrode of each electrical stimulation circuit are located on the same side of the frame.

FIG. 22 shows a schematic representation of the electrical fields 162 generated by two electrical stimulation circuits with two pairs of paracervical electrodes 110 positioned as shown in FIGS. 21A and 21B if the positive electrode and the negative electrode of each electrical stimulation circuit are located on the same side of the frame 104.

FIG. 23 shows a schematic representation of one of the two electrical fields generated by two electrical stimulation circuits with two pairs of paracervical electrodes 110 positioned as shown in FIGS. 21A and 21B if the positive electrode and the negative electrode of each electrical stimulation circuit are located on opposite sides of the frame 104. A representation of the second electrical field generated by the second electrical stimulation circuit is not shown to avoid confusion within the figure.

The External Controller and the IVES Control Application (the "IVES App")

FIG. 24 shows a high-level block diagram, illustrating by way of example, both the intravaginal components 101 and the external controller 103 according to certain embodiments of the present invention. As shown in FIG. 24, the external controller 103, which may comprise a tablet computer, a smart phone, a personal computer or any other type of computing or data communications device, includes a microprocessor 164, a volatile memory storage area for temporary storage of compiled and executable program instructions suitable for execution on the microprocessor, a display screen 168, an input device 170, such as a keyboard or touchscreen, a static memory 172 for storing an application program, a battery 174 and a radio frequency transceiver 176. The radio frequency transceiver 176 is configured to establish a wireless communication channel 182 with the radio frequency transceiver 138 inside the IVC 102. The static memory 172 stores the programming instructions for the IVES app 160. When executed by the microprocessor 164 on the external controller 103, the programming instructions in the IVES app 160 will cause the microprocessor 164 on the external controller 103 to communicate with the microprocessor 132 inside the IVC 102 via the wireless data communications channel 182 established between the two radio frequency transceivers.

The User Interface

A user interface module 180 in the IVES app 160 is configured to receive operating instructions from the user, which permits the user to activate, adjust and tune the electrical stimulation being delivered by electrical stimulation generator 130 to the paracervical electrodes 110, as well as other settings 184 available for changing using the user interface module 180. Thus, the user can manipulate controls on a display screen 168 of the external controller 103 (such as digital representations of buttons, icons and sliders) in the user interface on the external controller 103 to select, personalize, optimize, adjust, activate and/or deactivate the electrical stimulation provided to the pelvic and paracervical nerves by the IVES device 100. In addition, the radio frequency transceiver 176 and the microprocessor 164 inside the external controller 103 can receive over the wireless communication channel 182 status indicators 183 and other data generated by the microprocessor 132 connected to the printed circuit board 126 inside the shell 116 of the IVC 102, and/or data stored in the memory 134 on the printed circuit board 126 inside the shell 116 of the IVC 102. The status information 183 and other data may be displayed on the display screen 168 associated with the external controller 103 via the user interface. Preferably, the user interface module 180 of the IVES app 160 running on the external controller 103 also includes program instructions configured to permit the external controller 103 or the user to use email, text messages and/or another data or information transmitting processes to send the status information 184 and other data retrieved from the memory 134 of the IVC 102 to other devices, organizations or people, such as, for example, the user's personal physician or other health care provider.

Preferably, the IVES app 160 stored in the memory storage area 172 of the external controller 103 also includes program instructions that permit the external controller 103 to periodically query a remote computer system or server 178 to determine (1) whether any program updates associated with the IVES app 160 running on the external controller 103 are available, and/or (2) whether operating system updates, local program updates or firmware updates associated with the local control program 136 stored in the memory 134 of the IVC 102 are available. If such an update is available, the IVES app 160 is configured to automatically download and install it on the external controller 103, on the IVC 102, and/or both. By downloading such updates as they become available, the IVES app 160 running on the external controller 103, as well as the operating system, local control program 136 and firmware running on the IVC 102 will automatically remain substantially up-to-date with the latest bug fixes and/or improvements. In some embodiments, the IVES app 160 may be configured to prompt the user for permission or confirmation before downloading and/or installing program, operating system or firmware updates.

In preferred embodiments, the user may also select and activate a previously saved electrical stimulation profile (ESP) or a newly created ESP, which can then be saved to the memory 134 on the IVC 102. Once these operating instructions and parameters and preferred settings have been entered and saved on the external controller 103 using the user interface module 180, the microprocessor 164, still operating under the control of the IVES app 160, activates the radio frequency transceiver 176 to establish a wireless data communications link 182 with the radio frequency transceiver 138 inside the cylindrical shell 116 of the IVC 102. Then the microprocessor 164 uses the wireless data communications link 182 to transmit the operating parameters and preferred settings to the memory 134 inside the IVC 102. The IVES app 160 may also contain program instructions that, when executed by the microprocessor 164, will cause the microprocessor 164 to upload the status information 183 from the IVC 102 and show the status information 183 on the display screen 168. The status information 183 may include, for example, the amount of battery power remaining on the rechargeable battery 128 attached to the printed circuit board 126 of the IVC 102.

FIGS. 25A, 25B, 26A, 26B, 27A, 27B, 28A, 28B, 29A and 29B show, by way of example, a collection of user interface screenshots that might be used to operate, control and modulate IVES devices in accordance with an embodiment of the present invention. As shown in these figures, the display screen 168 communicatively connected to the user interface module 180 comprises a multiplicity of icons, buttons and sliders configured to control the operation of the IVES device 100 by sending the appropriate control signals over the wireless communication channel via the radio frequency radios inside the external controller and the IVC 102.

Figure 25B:
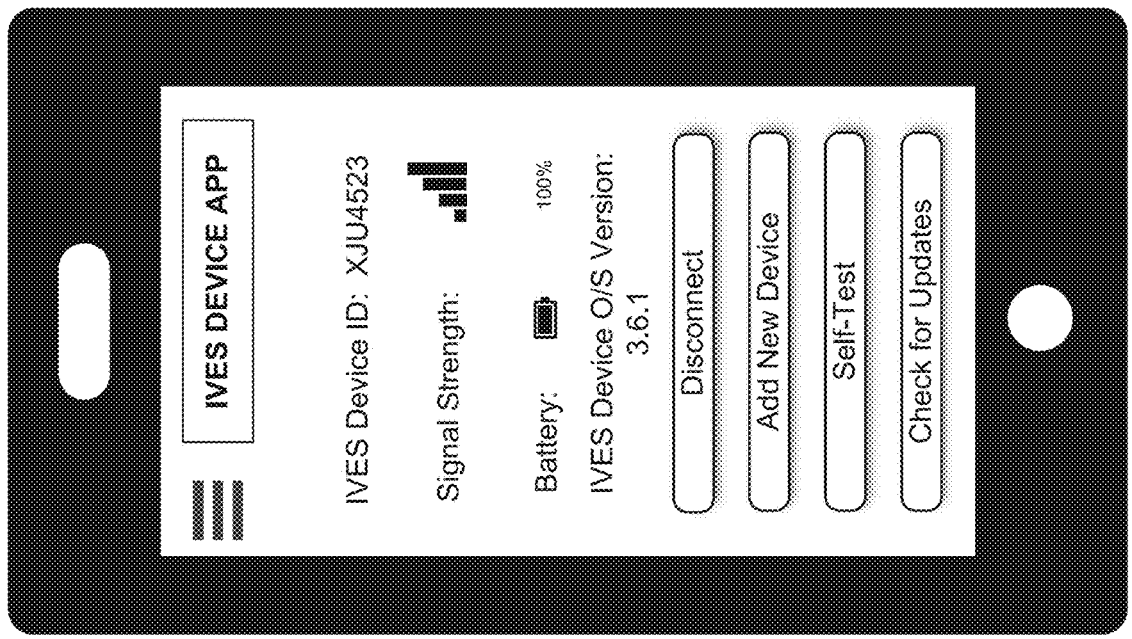
FIGS. 25A, 25B, 26A, 26B, 27A, 27B, 28A, 28B, 29A and 29B show, by way of example, a collection of user interface screenshots that might be used to activate, deactivate, operate, control and modulate the output of IVES devices constructed in accordance with an embodiment of the present invention.
Figure 25A:
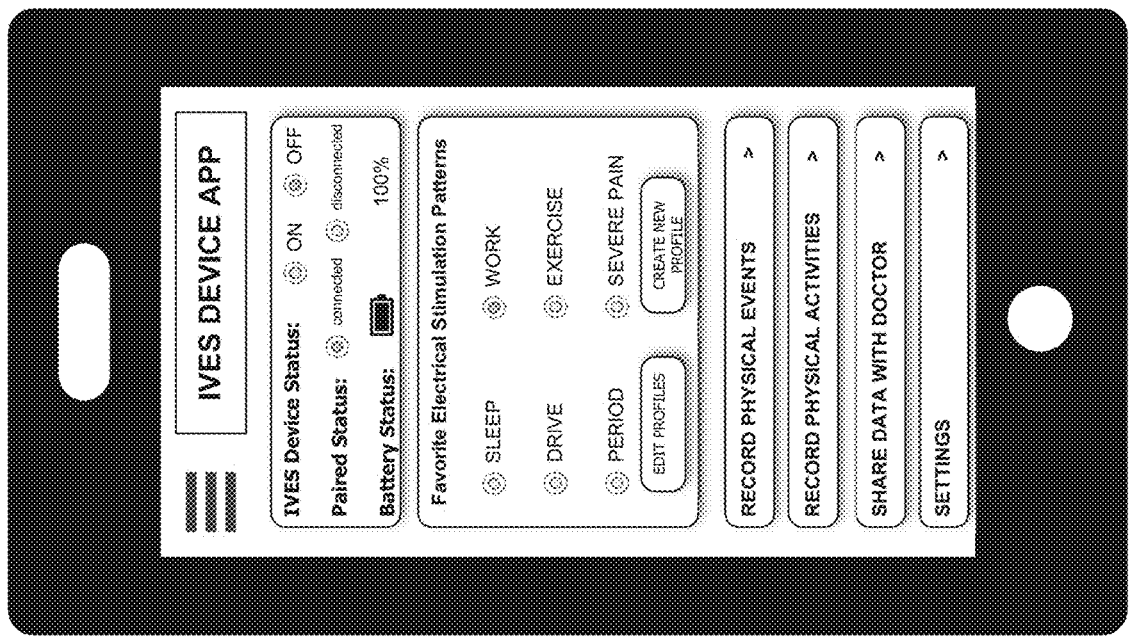
Figure 26B:
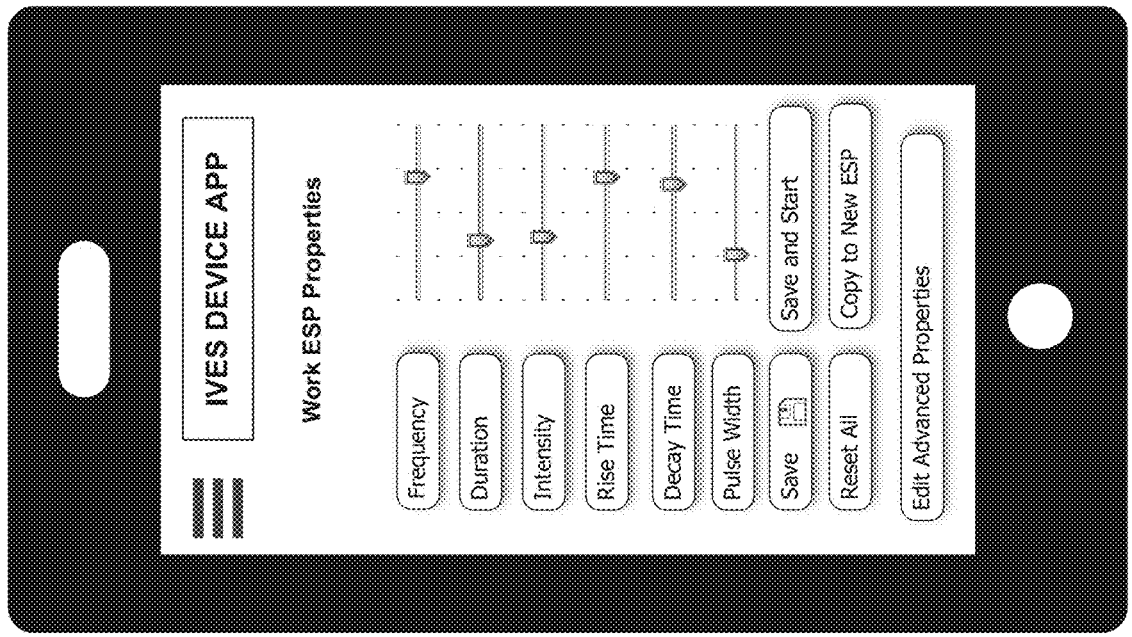
Figure 26A:
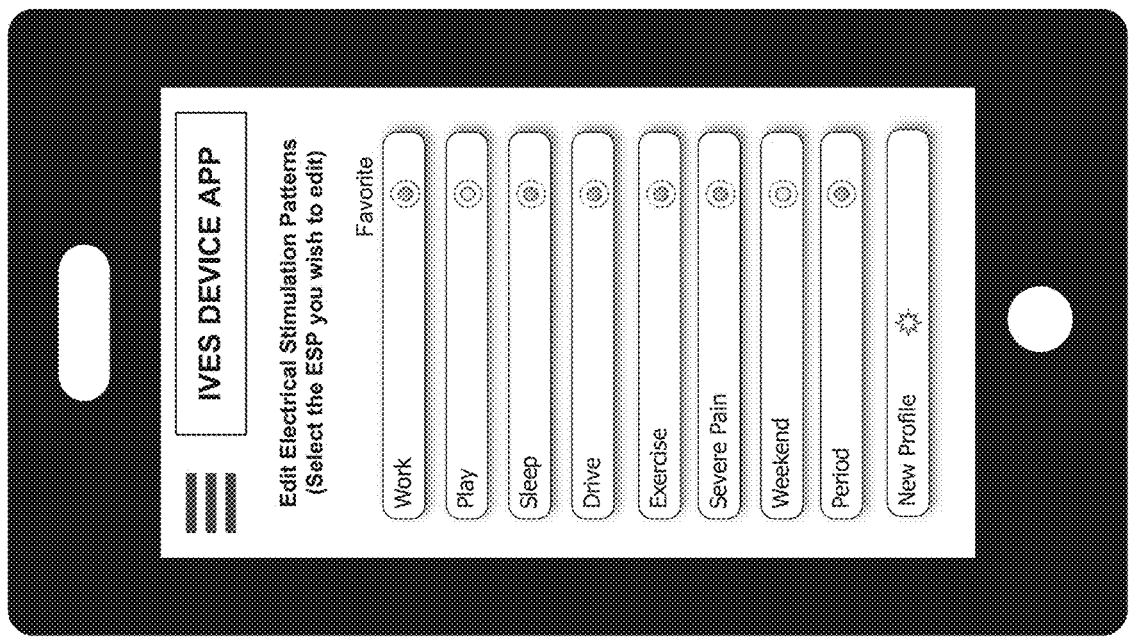
Figure 27B:
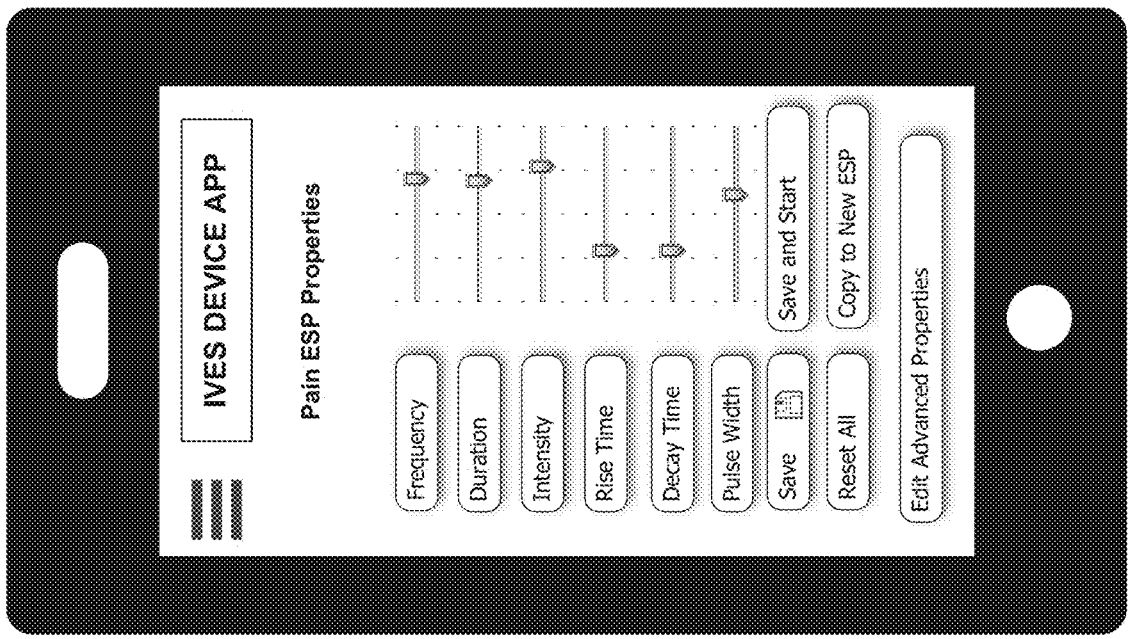
Figure 27A:
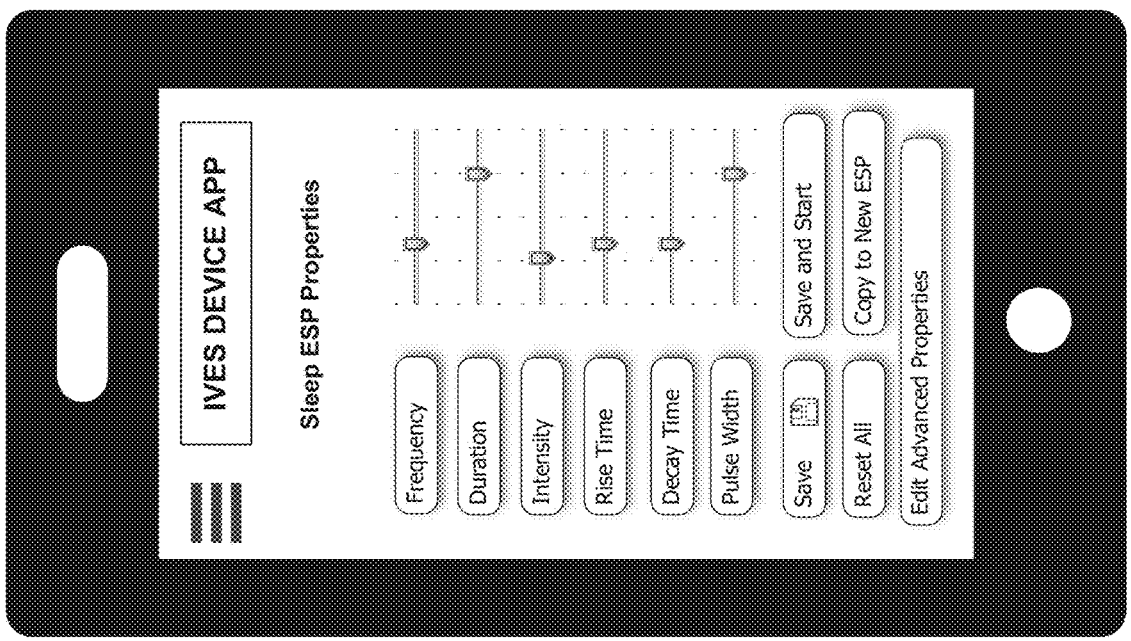

Among other things, the user interface may be programmed to provide a variety of useful functions, including but not limited to:

[1] Switching the IVES device on and off (FIG. 25A—"on/off" radio buttons).
[2] Displaying the current operating status and battery charge level for the IVES device (FIGS. 25A and 25B).
[3] Warning the patient when the battery charge level is low (FIGS. 25A and 25B).
[4] Permitting the patient to choose an electrical stimulation profile (ESP) from a number of "favorited" profiles, which may be (i) pre-loaded into the app during her initial consultation with her IVES practitioner based upon the patient's medical history and the prior treatment experiences of a multiplicity of other users, (ii) loaded into the app following consultations with her IVES practitioner based her experiences using the IVES device, or (iii) self-created and saved by the patient (FIG. 26A). Each ESP is a predefined combination of specific setting values. The patient may choose her desired ESP with the touch of a button or icon. For example, the patient may have learned that one ESP works best for her while she is at work, a second ESP works best for her when she is at home in the evenings, a third ESP works best for her when she goes to bed, and yet another ESP works best for her when she's exercising. In some embodiments, the data defining the patterns for the ESP's are stored only in the memory of the external controller. In other embodiments, the data defining the patterns for the ESP's may be stored only in the memory of the IVC 102, where they are indexed so that they can be activated by reference to the index number. In still other embodiments, the data defining the patterns for the ESP's are stored in the memories of both the external controller and the IVC 102.

[5] Permitting the patient to create, select, edit and save a variety of different operating properties, such as frequency, intensity, duration, intensity, rise time, decay time and stimulation width of an electrical stimulation session. (FIGS. 26A, 26B, 27A and 27B). Optionally, the patient may also be allowed to adjust advanced settings, such as voltage, amperage and/or waveform to be used during an electrical stimulation session, and anonymously upload her saved ESP properties to a community server, where they may be anonymously accessed and/or downloaded by other users.

Figure 28B:
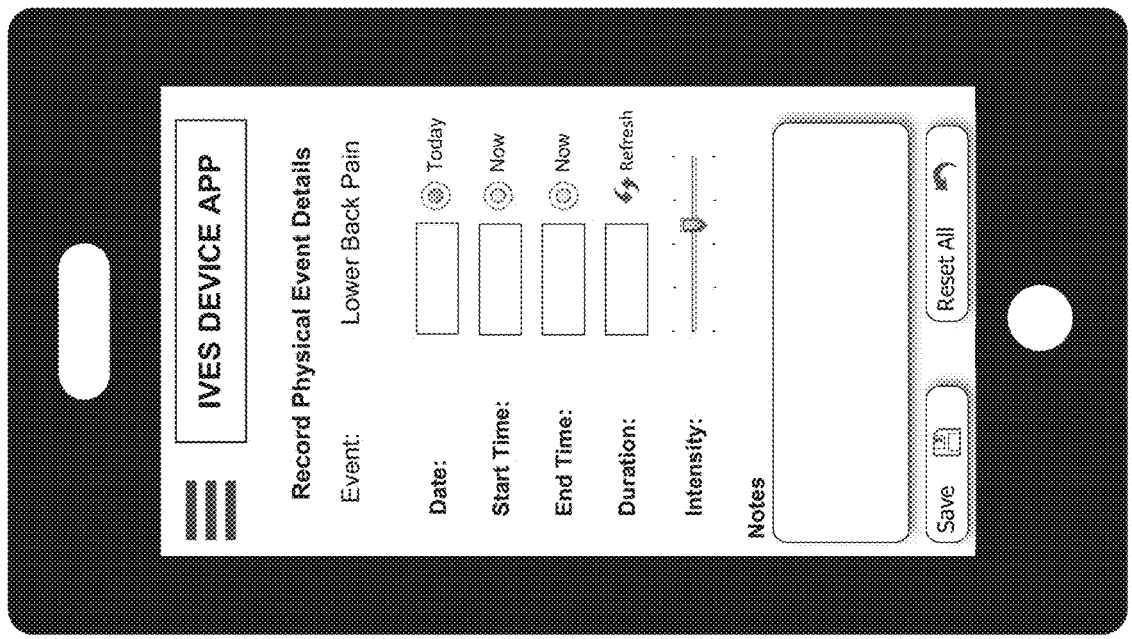
Figure 28A:
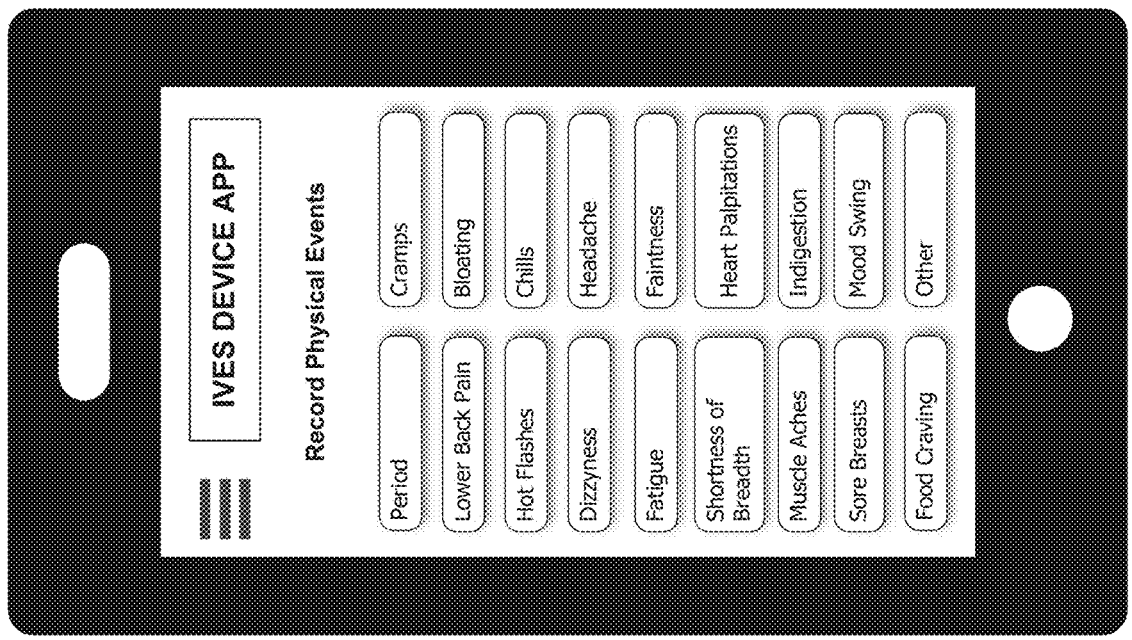

[6] Permitting the patient to track the starting times and ending times of certain physical events in her body, such as the beginning and end of a menstruation period, the beginning and end of menstruation cramps or backaches, the beginning and end of hot flashes or chills, etc., as well as potential side effects or complications that may be associated with the use of the IVES device. (FIGS. 28A and 28B). Suitably, all of the physical event information is stored in the memory of the external controller, automatically synced with the starting and ending times of electrical stimulation sessions (as well as all the settings and properties associated with the sessions), and subsequently uploaded to a computer system operated by herself or her physician or other healthcare provider for subsequent detailed analysis and evaluation of the performance and effectiveness of the IVES device during those events.

Figure 29B:
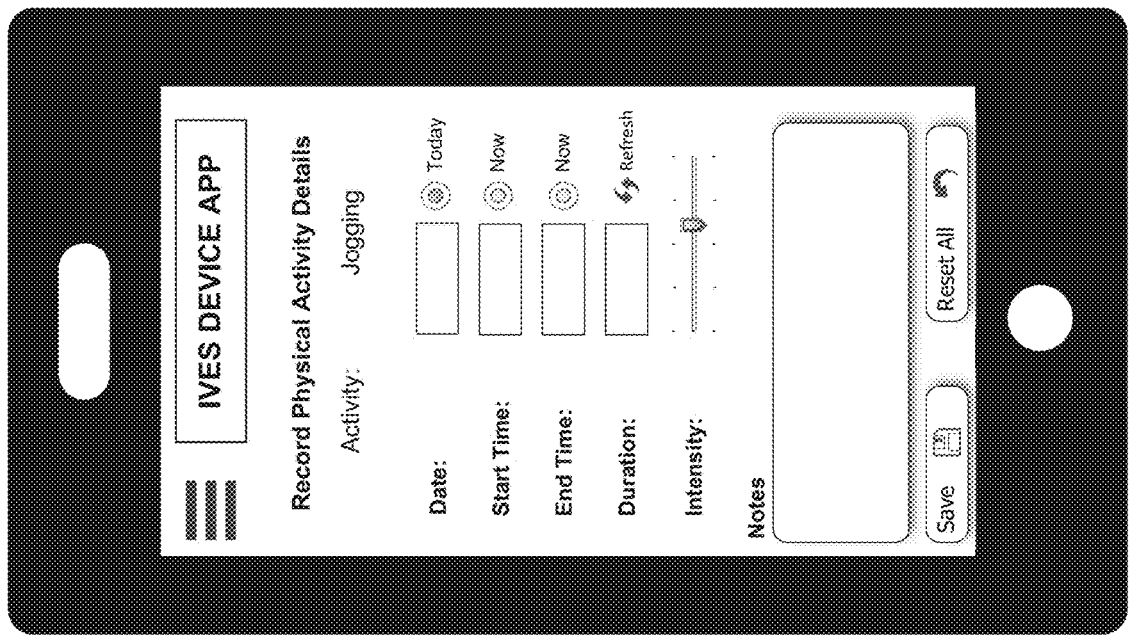
Figure 29A:
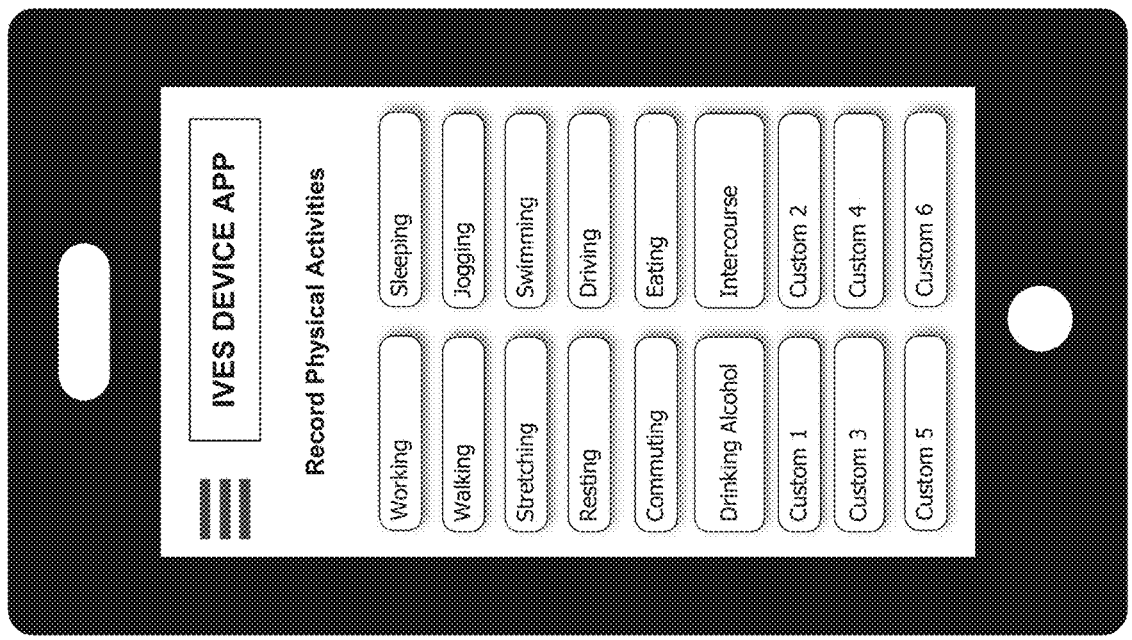

[7] Permitting the patient to track the starting times and ending times of certain physical activities, such as the beginning and end of a physical workout, the beginning and end of intercourse, etc. (FIGS. 29A and 29B). Suitably, all of the physical activity information is also saved in the memory of the external controller, automatically synced with the starting and ending times of electrical stimulation sessions (as well as all the settings and properties associated with the sessions) and the patients response to IVES treatment, and subsequently uploaded to a computer system operated by herself or her physician or other healthcare provider for subsequent detailed analysis and evaluation of the performance and effectiveness of the IVES device during those events.

[8] Permit the patient to automatically send physical event data and physical activity data to her practitioner. (FIG. 25A—"Share Data with Doctor" button).

[9] Permitting the patient to set up and transmit to the local control program on the circuit board of the IVES device a predefined schedule for the IVES device to automatically start and stop a series of electrical stimulation sessions (not shown in the figures).

[10] Whenever an electrical stimulation session is about to begin, providing an audible or visual alert on the patient's control or smart phone so that the patient is not surprised by unexpected vaginal stimulation, if any, and will have sufficient time to cancel the session or deactivate the IVES device if the timing of the session is inappropriate for whatever activity in which the patient is currently engaged (not shown in the figures).

[11] At the beginning, during and after an electrical stimulation session, providing an audible or visual alert on the patient's control or smart device, along with a prompt to the patient to use a slider or button on the user interface to rate on a scale her current level of pelvic pain and/or discomfort, so that this information can also be tracked, stored and subsequently uploaded to another computer system for detailed analysis and evaluation (not shown in the figures).

[12] Permitting the patient to update the IVES app by checking for available updates on remote computer system and, if any such updates are available, automatically downloading and installing those updates on the external controller (FIG. 25B—"Check for Updates" button).

Protocols for Using the IVES Device

It is anticipated that IVES devices constructed in accordance with certain embodiments of the present invention will be available to obtain from medical practitioners who are familiar with the causes and treatments of pelvic pain, female anatomy and physiology. These practitioners are preferably specifically trained on the custom fitting of the IVES devices, the use of electrical stimulation for the treatment of pelvic pain and the proper programming of settings for individual patients using the IVES device. Medical practitioners with the above-mentioned knowledge and training will hereinafter be referred to as "IVES Practitioners."

Evaluation of Candidates for the IVES Device

Appropriate candidates for using IVES devices according to the present invention include, but are not limited to, women with a documented history of endometriosis, dysmenorrhea, dyspareunia or chronic pelvic pain that is not associated with the presence of abdominal or pelvic malignancy. Prior to providing a woman with a device, she should have a complete gynecological examination including a pelvic examination and appropriate screening for cervical dysplasia or cancer and vaginal or pelvic infections. In addition, she should not have any contraindications to the use of electrical stimulation such as the presence of a pacemaker.

Initial Fitting of the Device by an IVES Practitioner

Because every woman's pelvic anatomy is unique and the goal of treatment with the IVES device is to comfortably apply electrical stimulation to the pelvic and paracervical nerves beneath the paracervical vaginal epithelium in the areas of the lateral vaginal fornices, it is important that users of the device be properly fitted for its proper use.

Proper fitting of the intravaginal components 101 of the IVES device 100 requires the selection of a frame 104 that is the appropriately sized for the patient with adjustment made to the shape of the frame 104 if indicated.

Initial Programming of the Device

It is anticipated that individual patients will have several optimal Electrical Stimulation Profiles (ESP's) for the electrical stimulation that is delivered by the IVES device for different circumstances. Circumstances such as activity, time of day, the presence or absence of stress and the level of pelvic pain being experienced by the patient make one ESP preferable over another from time to time. The settings established in each ESP may include adjustments to a variety of parameters such as electrical intensity, stimulation frequency, electrical stimulation waveform, duration of treatment and others.

The initial ESP's made available to the patient may be established in consultation with her IVES practitioner based upon the patient's medical history and the aggregated experiences of numerous patients using the IVES device.

During her initial consultation with an IVES practitioner, the patient will receive an introduction to the use of the IVES device, the external controller, the IVES app, the initially available ESPs, the sensations and feelings that should be avoided during the use of the IVES device and method of recording events through the IVES app.

During the initial consultation or a subsequent one, the patient will receive instruction regarding the creation of "personalized" user defined ESP's created and made available to her through the IVES app.

While the present invention has been disclosed with reference to certain embodiments, numerous modifications, alterations and changes to the disclosed embodiments are possible without departing from the scope of the present invention, as defined in the appended claims. Accordingly, it is not intended that the present invention be limited to the described embodiments, but that it has the full scope defined by the language of the following claims, and equivalents thereof.

What is claimed is:

1. A device for treating pelvic pain in a female patient, comprising:
    a set of intravaginal components including a frame having a distal portion and a proximal portion, the frame being configured so that when the set of intravaginal components are inserted into the vagina of the female patient, the proximal portion of the frame will be in contact with the paracervical vaginal epithelium of the posterior and the lateral vaginal fornices of the female patient;
    one or more pairs of paracervical electrodes embedded in a surface material covering the proximal portion of the frame;
    an intravaginal capsule comprising distal end, a proximal end, a microprocessor, a memory and an electrical stimulation generator;
    an electrode plug that plugs into the intravaginal capsule to establish an electrical connection with the electrical stimulation generator; and
    one or more connecting wires that electrically couple the electrode plug to said one or more pairs of paracervical electrodes; and
    a local control program in the memory comprising program instructions that, when executed by the microprocessor, will cause the microprocessor to generate and send control signals to the electrical stimulation generator, the control signals configured to cause the electrical stimulation generator to generate and transmit low voltage electrical current to the one or more pairs of paracervical electrodes via said electrode plug and said one or more connecting wires;
    wherein the low voltage electrical current received by the one or more pairs of paracervical electrodes creates an electrical field that passes through the paracervical vaginal epithelium of the posterior and the lateral vaginal fornices of the female patient, and thereby neuromodulate neural structures in the pelvis.

2. The device of claim 1, wherein the neural structures neuromodulated by the electrical field include the pelvic and paracervical nerves in the pelvis of the female patient.

3. The device of claim 2, wherein the pelvic and paracervical nerves neuromodulated by the electrical field include nerves that innervate the uterus of the female patient.

4. The device of claim 2, wherein the pelvic and paracervical nerves neuromodulated by the electrical field include nerves that innervate the upper vagina and cervix of the female patient.

5. The device of claim 1, further comprising:
    a sling attached to the frame; and
    a pouch molded into the sling;
    wherein the pouch is configured to receive and hold the distal end of the intravaginal capsule.

6. The device of claim 1, further comprising:
    a first radio frequency transceiver located inside the intravaginal capsule; and
    program instructions in the local control program that, when executed by the microprocessor, will cause the microprocessor to cause the first radio frequency transceiver to establish a data communications channel with an external controller and to receive, via the data communications channel, a remote-control instruction to control operation of the electrical stimulation generator in the intravaginal capsule.

7. The device of claim 6, further comprising the external controller.

8. The device of claim 7, wherein the external controller comprises a second radio frequency transceiver configured to transmit the remote-control instruction from the external controller to the first radio frequency transceiver located inside the intravaginal capsule.

9. The device of claim 7, wherein:
    the external controller further comprises a second microprocessor and a memory storage area;
    the memory storage area stores a remote-control application and an electrical stimulation pattern; and
    the remote control application comprises program instructions that, when executed by the second microprocessor on the external controller, will cause the second microprocessor to send a control signal to the microprocessor inside the intravaginal capsule, the control signal being configured to cause the microprocessor in the intravaginal capsule to cause the electrical stimulation generator to generate and transmit electrical stimulation that corresponds to the electrical stimulation pattern stored in the memory of the external controller.

10. The device of claim 9, wherein the local control program on the external controller further comprises a user interface module, stored in the memory storage area on the external controller, the user interface module having program instructions that, when executed by the second microprocessor on the external controller, will cause the second microprocessor to receive an operating instruction from the female patient.

11. The device of claim 10, wherein the user interface module further comprises program instructions that, when executed by a second microprocessor on the external controller, will cause the second microprocessor to:
    prompt the female patient to select a set of properties for a user-defined electrical stimulation pattern;
    save the set of properties in the memory storage area as a predefined electrical stimulation pattern; and
    send a control signal to the microprocessor inside the intravaginal capsule which will cause the microprocessor to run the electrical stimulation generator in accordance with said predefined electrical stimulation pattern.

12. The device of claim 10, wherein the user interface module stored in the memory storage area on the external controller further comprises program instructions that, when executed by a second microprocessor on the external controller, will cause the second microprocessor to:
    retrieve a current operating status from the intravaginal capsule via the first radio frequency transceiver and the data communication channel; and
    display the current operating status on a display screen connected to the external controller.

13. The device of claim 1, further comprising a wireless rechargeable battery configured to provide electric power to the microprocessor and the electrical stimulation generator.

14. The device of claim 1, further comprising a socket in the proximal end of the intravaginal capsule, the socket being configured to receive and hold the electrode plug.

15. The device of claim 14, further comprising a male electrical connector, located at the distal end of the socket, that is electrically coupled with an electrical contact inside the intravaginal capsule, the electrical contact being electrically coupled to the electrical stimulation generator.

16. A device for treating pelvic pain in a female patient, the device comprising:
- a frame;
- a sling connected to the frame;
- an intravaginal capsule attached to the sling, the intravaginal capsule comprising a microprocessor, a memory, a local application program stored in the memory and an electrical stimulation generator;
- a socket in the intravaginal capsule, the socket having a distal end and a base at the distal end;
- a pair of electrode units, each electrode unit in the pair of electrode units comprising an electrical contact on the electrical stimulation generator, a male electrical contact located in the base of the socket and configured to make electrical connection to the electrical contact on the electrical stimulation generator, an electrode plug configured to be plugged into the socket, and a female electrical contact embedded in the electrode plug and configured to make another electrical connection with the male electrical contact when the electrode plug is plugged into the socket in the intravaginal capsule;
- one or more pairs of paracervical electrodes configured for placement within the lateral vaginal fornices of the female patient; and
- one or more connecting wires that extend from the female electrical contact to said one or more pairs of paracervical electrodes;
- wherein the local application program comprises programming instructions that, when executed by the microprocessor, will cause the microprocessor to transmit control signals to the electrical stimulation generator to make the electrical stimulation generator transmit electrical current to said one ore more pairs of paracervical electrodes via said one or more connecting wires;
- whereby, the electrical current produces an electrical field around said one or more pairs of paracervical electrodes so that the electrical field passes through the lateral vaginal fornices of the female patient to neuromodulate neural structures of the pelvis of the female patient.

17. The device of claim 16, wherein the neural structures neuromodulated by the electrical field include the pelvic and paracervical nerves in the pelvis of the female patient.

18. The device of claim 16, wherein the pelvic and paracervical nerves neuromodulated by the electrical field include the nerves that innervate the uterus of the female patient.

19. The device of claim 16, wherein the pelvic and paracervical nerves neuromodulated by the electrical field include nerves that innervate the upper vagina and cervix of the female patient.

20. The device of claim 16, further comprising:
- a first radio frequency transceiver located inside the intravaginal capsule; and
- program instructions in the local control program that, when executed by the microprocessor, will cause the microprocessor to cause the first radio frequency transceiver to establish a data communications channel with an external controller and to receive, via the data communications channel, a remote-control instruction to control operation of the electrical stimulation generator in the intravaginal capsule.

21. The device of claim 20, further comprising the external controller.

22. The device of claim 21, wherein the external controller comprises a second radio frequency transceiver configured to transmit the remote-control instruction from the external controller to the first radio frequency transceiver located inside the intravaginal capsule.

* * * * *